United States Patent
Dickman et al.

(10) Patent No.: US 10,399,920 B2
(45) Date of Patent: Sep. 3, 2019

(54) CRYSTALLINE FORM OF CANNABIDIOL

(71) Applicants: Daniel Dickman, San Ramon, CA (US); Daniel Levin, La Canada, CA (US)

(72) Inventors: Daniel Dickman, San Ramon, CA (US); Daniel Levin, La Canada, CA (US)

(73) Assignee: S&B Pharma, Inc., Azusa, CA (US)

( * ) Notice: Subject to any disclaimer, the term of this patent is extended or adjusted under 35 U.S.C. 154(b) by 36 days.

(21) Appl. No.: 15/609,228

(22) Filed: May 31, 2017

(65) Prior Publication Data

US 2017/0349518 A1 Dec. 7, 2017

Related U.S. Application Data

(60) Provisional application No. 62/344,045, filed on Jun. 1, 2016.

(51) Int. Cl.
*C07C 39/23* (2006.01)

(52) U.S. Cl.
CPC .......... *C07C 39/23* (2013.01); *C07B 2200/13* (2013.01); *C07C 2601/16* (2017.05)

(58) Field of Classification Search
CPC .. C07C 39/23; C07C 2601/16; C07B 2200/13
See application file for complete search history.

(56) References Cited

U.S. PATENT DOCUMENTS

| | | | |
|---|---|---|---|
| 7,674,922 B2 | 3/2010 | Burdick et al. | |
| 9,125,859 B2 | 9/2015 | Whalley et al. | |
| 2003/0017216 A1 | 1/2003 | Schmidt et al. | |
| 2006/0167283 A1 | 7/2006 | Flockhart et al. | |
| 2010/0298579 A1 | 11/2010 | Steup et al. | |

FOREIGN PATENT DOCUMENTS

| | | |
|---|---|---|
| WO | WO9952524 | 10/1999 |
| WO | WO2006053766 A1 | 5/2006 |
| WO | WO2013038157 A1 | 3/2013 |

OTHER PUBLICATIONS

Adams (Journal of the American Chemical Society; 1940, vol. 62, 196-200).*
Adams et al., "Isolation of Cannabinol, Cannabidiol and Quebrachitol from Red Oil of Minnesota Wild Hemp," Journal of the American Chemical Society, vol. 62, pp. 2194-2196 (1940).
Jones et al., "Cannabidiol," Acta Cryst., B33, pp. 3211-3214 (1977).
Wilner, "Marijuana for Epilepsy: Weighing the Evidence," Medscape. com, (Mar. 25, 2014).
National Bureau of Standards Monograph 25, Section 16, pp. 111-113, Library of Congress Catalog Card No. 53-61386 (1979).

* cited by examiner

*Primary Examiner* — Pancham Bakshi
(74) *Attorney, Agent, or Firm* — Sonapat LLC

(57) ABSTRACT

Crystalline Cannabidiol of a novel form, including (R,R)-(−)-crystalline Cannabidiol, as well as methods of making such novel form of Cannabidiol, pharmaceutical formulations comprising such novel form of Cannabidiol, and methods of treating diseases with such novel form of Cannabidiol.

16 Claims, 14 Drawing Sheets

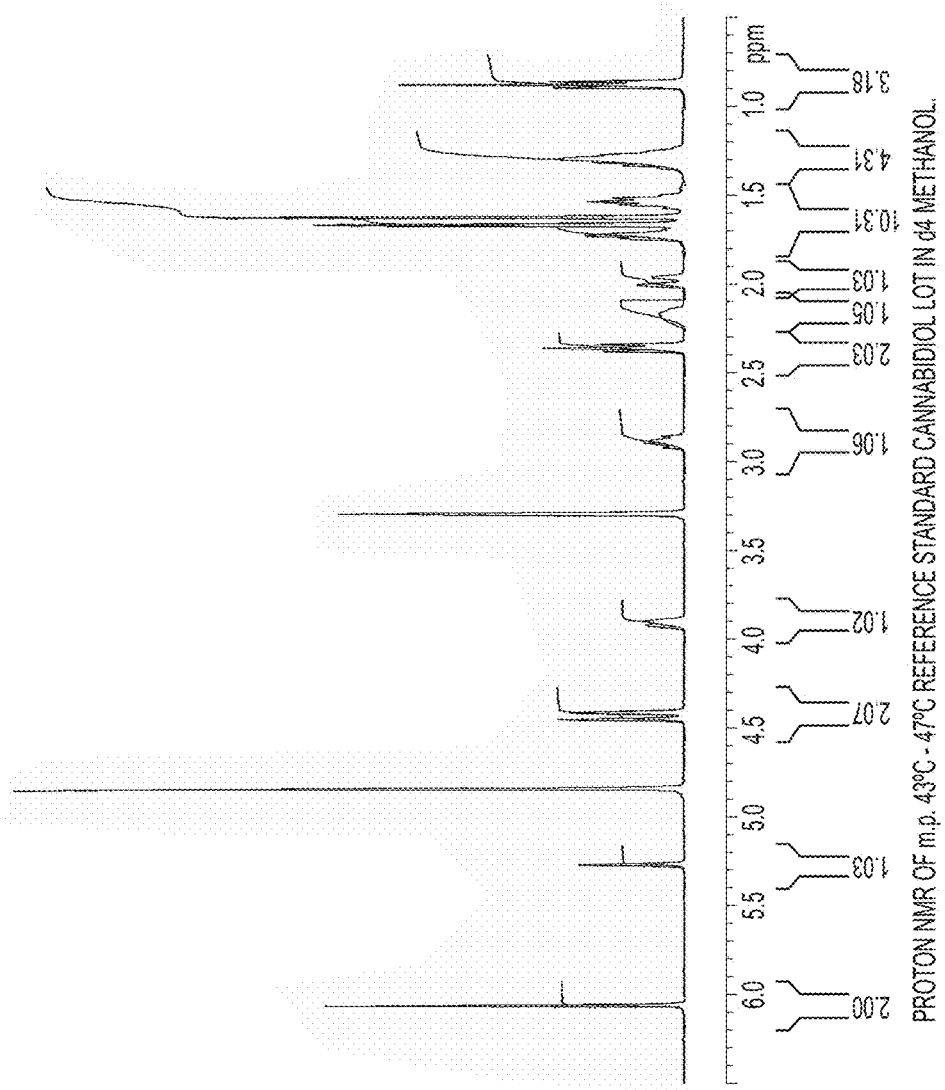

DSC OF THE PROPAGATED CRYSTALLINE LOT OF m.p. 43°C - 47°C CANNABIDIOL AT A HEATING RAMP RATE OF 1DEG/MIN. (DAD-004-180)

PEAK PICKED FTIR OF A CRYSTALLINE LOT OF m.p. 43°C - 47°C CANNABIDIOL PREPARED BY SEEDING WITH CANNABIDIVARIN.

CRYSTALLINE FORM OF CANNABIDIOL

This application claims benefit of U.S. Provisional Application No. 62/344,045, filed on Jun. 1, 2016, the entire contents of which are specifically incorporated by reference herein.

BACKGROUND

Cannabidiol is a cannabinoid found in Cannabis and was first described as a solid in the chemical literature by Roger Adams in the *Journal of the American Chemical Society*, 1940, V62, P2194-6 as having a melting point of 66° C.-67° C. In 1977, it was isolated as a solid by crystallization from pentane by Jones, Peter G: *Acta Cryst.* (1977) B33, P3211-3214 and was reported to have a melting point of 66° C.-67° C. as well. Cannabidiol is also isolated as an oil directly from the hemp plant and is converted to a white crystalline solid, m.p. 64° C.-66° C. by the process provided by Flockhart, et.al.: US2006/0167283, which also lists a literature value of the Cannabidiol melting point of 66° C.-67° C.

An orally-administered liquid containing Cannabidiol has received orphan drug status in the US, for the treatment of Dravet Syndrome (a form of epilepsy), under the (GW Pharma) brand name Epidolex (Wilner, A N; 25 Mar. 2014, "Marijuana for Epilepsy: Weighing the Evidence" *Medscape Neurology*). Cannabidiol is also a component of Namiximols (USAN, trade name Sativex), which is an aerosolized mist for an oral administration containing a near 1:1 ratio of Cannabidiol and THC. This drug was approved by Canadian authorities in 2005 to alleviate pain associated with multiple sclerosis. Cannabidiol has been suggested as an agent for the treatment of epilepsy as set forth in U.S. Pat. No. 9,125,859, the contents of which are incorporated herein by reference. It has also been proposed for use as an anti-inflammatory reagent WO 9952524 A1 19991021 and for treatment of cancer (WO 2013038157 A1). Cannabidiol is currently undergoing various clinical trials.

The new form of crystalline Cannabidiol described and claimed herein differs from the m.p. 66° C.-67° C. form, for example, in its XRPD pattern and by having a lower melting point. This new polymorph could be more advantageous in one or more respects compared to the other form, for example, in terms of easier, quicker and more extensive dissolution into solvents and more rapid bioavailability commensurate with the lower melting temperature, equating to a less thermodynamically stable and hence more soluble polymorph compared with the other form.

SUMMARY OF THE INVENTION

One embodiment includes a new form of crystalline Cannabidiol (such as crystalline (R,R)-(−)-Cannabidiol), wherein the new form has a melting point within the range of from about 37° C. to about 50° C., such as from about 39° C. to about 48° C., or from about 43° C. to about 47° C., or from about 43° C. to about 46° C.

Another embodiment includes a new form of crystalline Cannabidiol (such as crystalline (R,R)-(−)-Cannabidiol) having a powder x-ray diffraction pattern comprising a peak at about 10.7° 2θ, such as for crystalline Cannabidiol having a melting point within the ranges described in the previous embodiment.

Another embodiment includes the crystalline Cannabidiol having a powder x-ray diffraction pattern comprising a peak at one or more of the following positions: about 14.8° 2θ, about 21.4° 2θ, about 29.9° 2θ and about 21.2° 2θ.

The crystalline Cannabidiol may also be characterized in certain embodiments as having a differential scanning calorimetry thermogram comprising a maximum endotherm at from about 43° C. to about 47° C. (such as from about 43° C. to about 45° C.), wherein the differential scanning calorimetry thermogram has a temperature ramp rate of about 1° C. per minute; or as having an FT-IR spectrum comprising a peak at one or more of the following positions: about 658 $cm^{-1}$, about 890 $cm^{-1}$, about 1026 $cm^{-1}$, about 1433 $cm^{-1}$, about 1585 $cm^{-1}$, about 1628 $cm^{-1}$ and about 2926 $cm^{-1}$.

Additional embodiments include the new form of crystalline (R,R)-(−) Cannabidiol that is substantially pure, pharmaceutical formulations comprising the new form of crystalline Cannabidiol, and methods of treating epilepsy, cancer, pain or inflammation with the new form of crystalline Cannabidiol.

Further embodiments include processes for making the new form of crystalline Cannabidiol by seeding with crystals of the new form or by seeding with a form of crystalline Cannabidivarin.

Amorphous Cannabidiol, amorphous (R,R)-(−) Cannabidiol, substantially pure amorphous (R,R)-(−) Cannabidiol, pharmaceutical formulations comprising the amorphous Cannabidiol and the methods of treatment disclosed above with amorphous Cannabidiol form additional embodiments.

BRIEF DESCRIPTION OF THE DRAWINGS

FIG. 2 is a non-peak-picked $^1$H-NMR spectrum of a solution of the new form of (R,R)-(−)-Cannabidiol in $d_4$ methanol.

DETAILED DESCRIPTION

Figure 1A:
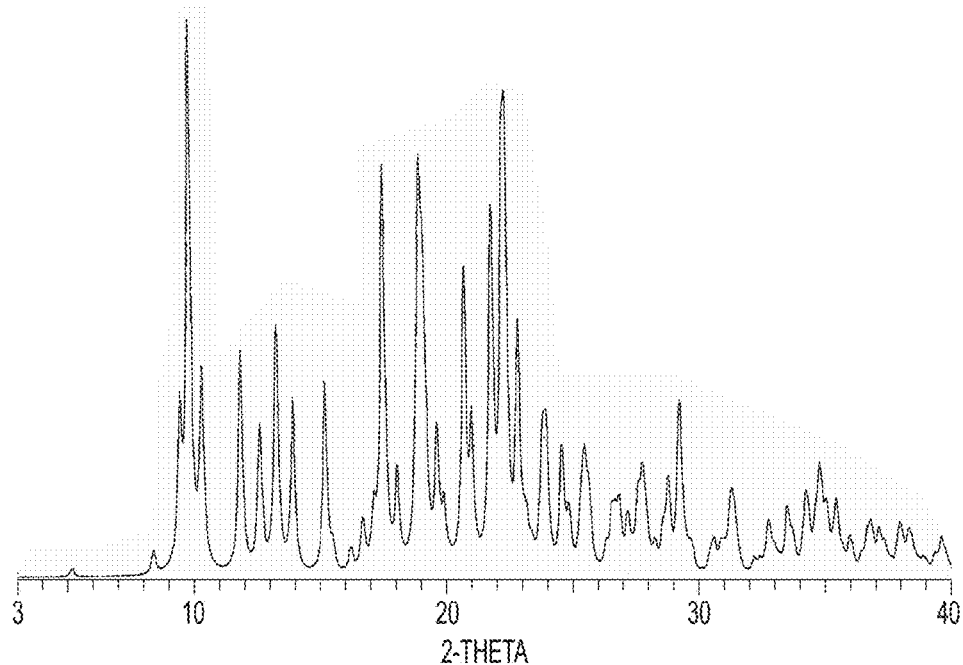
FIG. 1A is a computer generated XRPD pattern of a form of Cannabidiol (from FIG. 11), that melts at 66° C.-67° C.

The terms "crystalline" and "crystalline form" are often used to refer to a class or type of solid-state material which is crystalline as that term is commonly understood by those of skill in the pharmaceutical arts. Crystalline forms of compounds, such as active pharmaceutical ingredients, are often preferred over amorphous or other non-crystalline forms because of properties such as stability, ease of preparation and use, and ease of purification.

When using solid-state analytical methods to characterize crystalline forms, such methods typically rely on other information about the chemical identity of the form. For example, solution-state methods such as HPLC, and solution-state NMR as well as knowledge about starting materials and chemical synthesis procedures can supply sufficient information to identify the chemical composition of a material. Solution-state techniques are not used to characterize crystalline forms. To determine whether a material is crystalline, one can use thermal methods, x-ray diffraction, light microscopy or visual observation, for example.

Crystalline forms may also be characterized by reference to various techniques. Examples of solid-state techniques which may be used to characterize and/or analyze crystalline forms include x-ray powder diffraction ("XRPD"), thermal techniques such as differential scanning calorimetry ("DSC") and melting point with, for example, a melting point apparatus, and infrared spectroscopy, such as Fourier-Transform infrared spectroscopy ("FT-IR").

Those of ordinary skill in the art will recognize that there are often multiple ways, including multiple ways using the same analytical technique, to characterize crystalline forms. For example, one may find that a single x-ray powder diffraction peak may be used to characterize a crystalline form. Additional peaks could also be used, but are not necessary, to characterize such forms including an entire diffraction pattern. Although all the peaks within an entire diffractogram may be used to characterize a crystalline form, one may instead, and typically does, as disclosed herein, use a subset of that data to characterize such a crystalline form.

X-ray powder diffraction patterns are some of the most commonly used solid-state analytical techniques to characterize crystalline forms. An x-ray powder diffraction pattern is an x-y graph with ° 2θ (diffraction angle) on the x-axis and intensity on the y-axis. The peaks within this plot may be used to characterize a crystalline form. The data is often represented by the position of the peaks on the x-axis rather than the intensity of peaks on the y-axis because peak intensity can be particularly sensitive to sample orientation (see Pharmaceutical Analysis, Lee & Web, pp. 255-257 (2003)). Thus, intensity is not typically used by those skilled in the art to characterize crystalline forms.

As with any data measurement, there may be variability in x-ray powder diffraction data. In addition to the variability in peak intensity, there may be variability in the position of peaks on the x-axis. This variability can, however, typically be accounted for when reporting the positions of peaks for purposes of characterization. Such variability in the position of peaks along the x-axis derives from several sources. One comes from sample preparation. Samples of the same crystalline form when prepared under different conditions may yield slightly different diffractograms. Factors such as particle size, moisture content, solvent content, and crystal orientation may all affect how a sample diffracts x-rays. Another source of variability comes from varying instrument parameters among different x-ray diffractometers. Likewise, different software packages process x-ray data differently, and this also leads to variability. These and other sources of variability are known to those of ordinary skill in the pharmaceutical arts.

Due to such sources of variability, it is common to recite x-ray diffraction peaks using the word "about" prior to the peak value in degrees two theta which presents the data to within ±0.1 or ±0.2° 2θ of the stated peak value depending on the circumstances. All x-ray powder diffraction peaks cited herein have been reported with a variability on the order of ±0.2° 2θ whether modified with the term "about" or not.

Infrared spectroscopy, such as FT-IR, is another technique that may be used to characterize crystalline forms together with, or separately from, x-ray powder diffraction and/or other techniques. In an infrared spectrum, absorbed light is plotted on the x-axis of a graph in the units of "wavenumber" ($cm^{-1}$), with intensity on the y-axis. Variation in the position of the peaks also exists and may be due to sample conditions as well as data collection and processing. The typical variability in such spectra reported herein is on the order of ±2.0 $cm^{-1}$. Thus, the use of the word "about" when referencing infrared peaks is meant to include this variability and all infrared peaks disclosed herein are intended to be reported with such variability whether modified with the term "about" or not.

Thermal methods are often used to characterize crystalline forms. The melting point of a crystalline form, as measured by methods such as capillary melting point, DSC, or hot stage microscopy, alone or in combination with techniques such as x-ray powder diffraction, infrared spectroscopy, or both, may be used to characterize crystalline forms.

As with any analytical technique, melting point determinations are also subject to variability. Common sources of variability, in addition to instrumental variability, are due to colligative properties such as the presence of other crystalline forms or other impurities within a sample whose melting point is being measured. Other sources of variability include the rate of heating, and techniques used for measuring the melting point. To account for this variability, the melting point is frequently reported as being within a certain temperature range.

Figure 6:
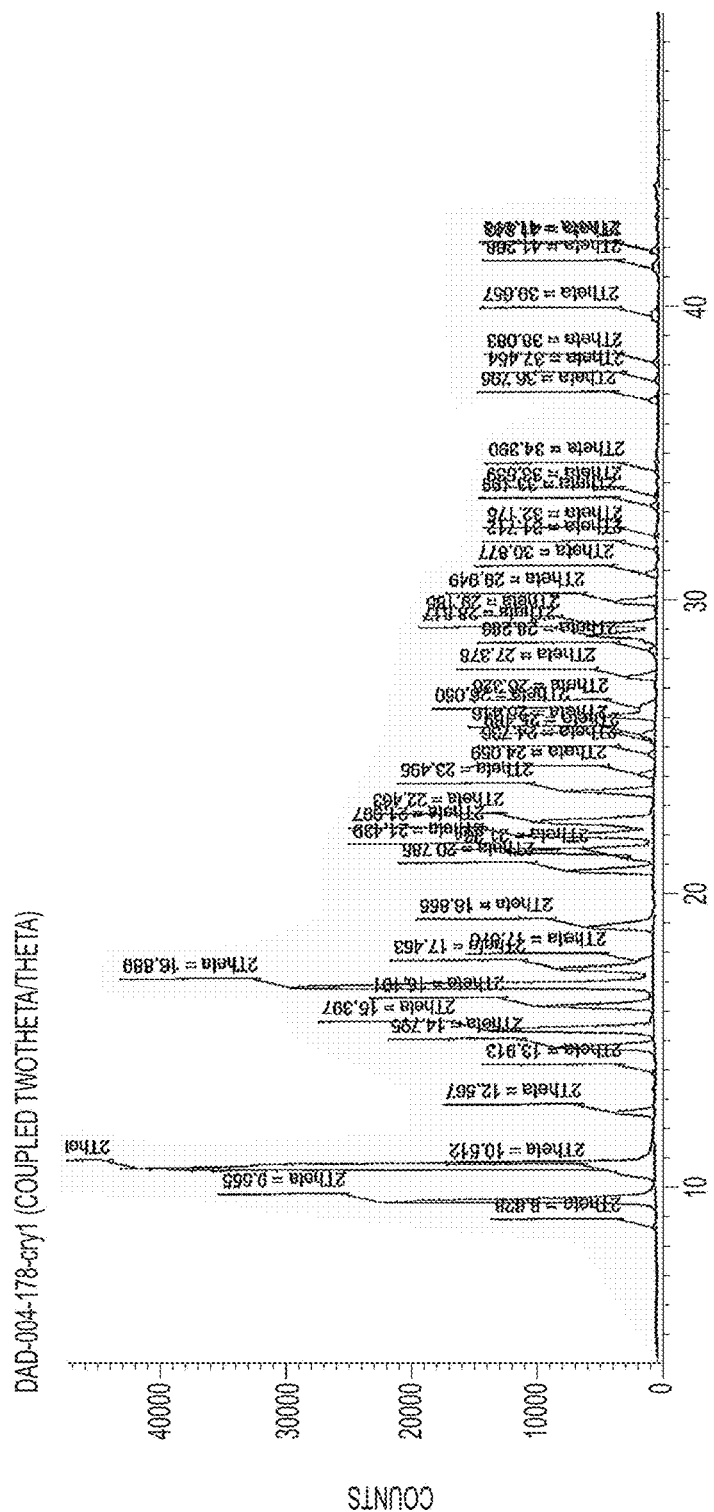
FIG. 6 is an x-ray powder diffraction pattern of the region from about 4° 2θ to about 50° 2θ of the new form of (R,R)-(−)-crystalline Cannabidiol prepared by seeding with Cannabidivarin, where the peaks are picked.
Figure 9:
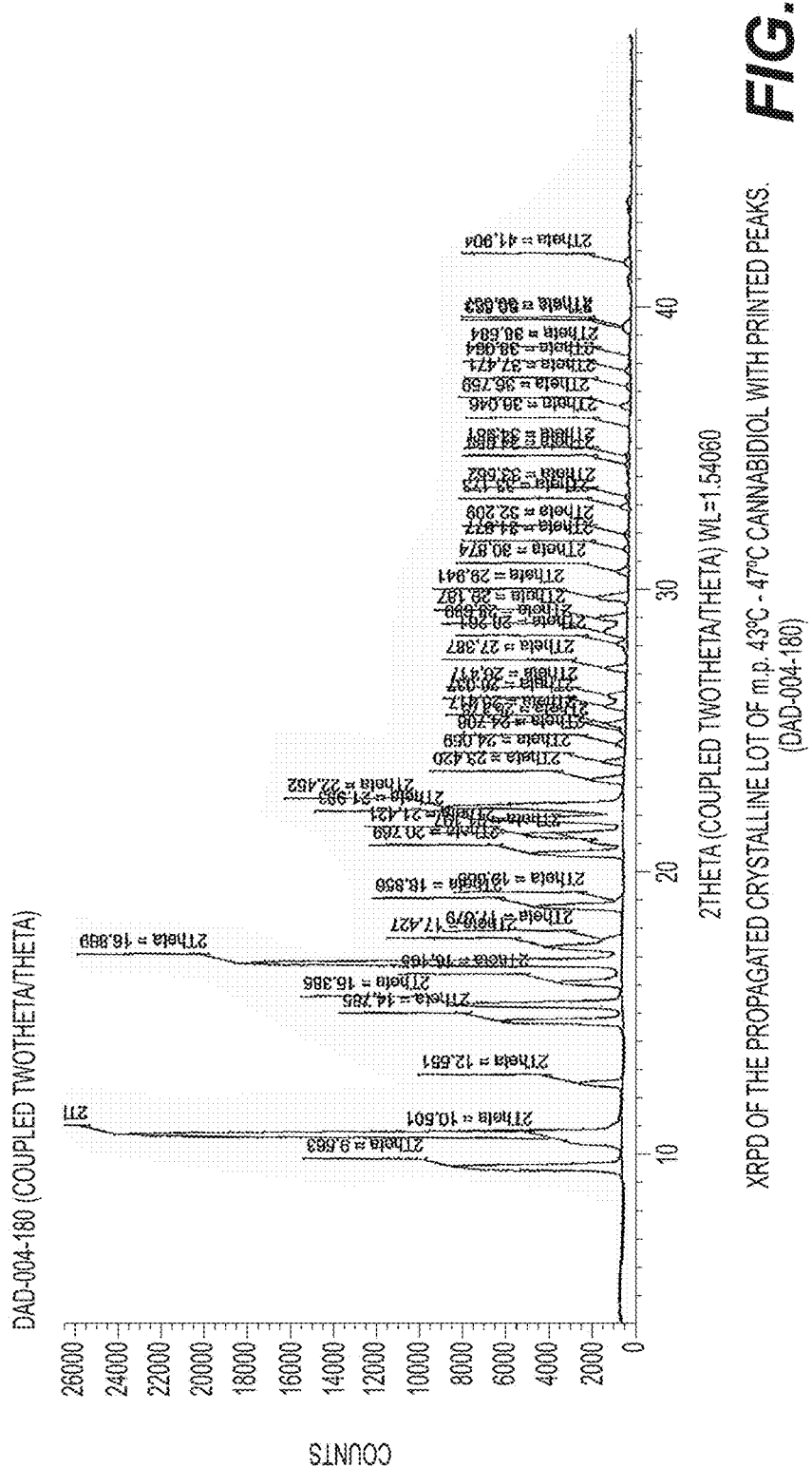
FIG. 9 is an x-ray powder diffraction pattern of the region from about 4° 2θ to about 50° 2θ of the new form of (R,R)-(−)-crystalline Cannabidiol prepared by seeding with the new form of Cannabidiol, where the peaks are picked.
Figure 10:
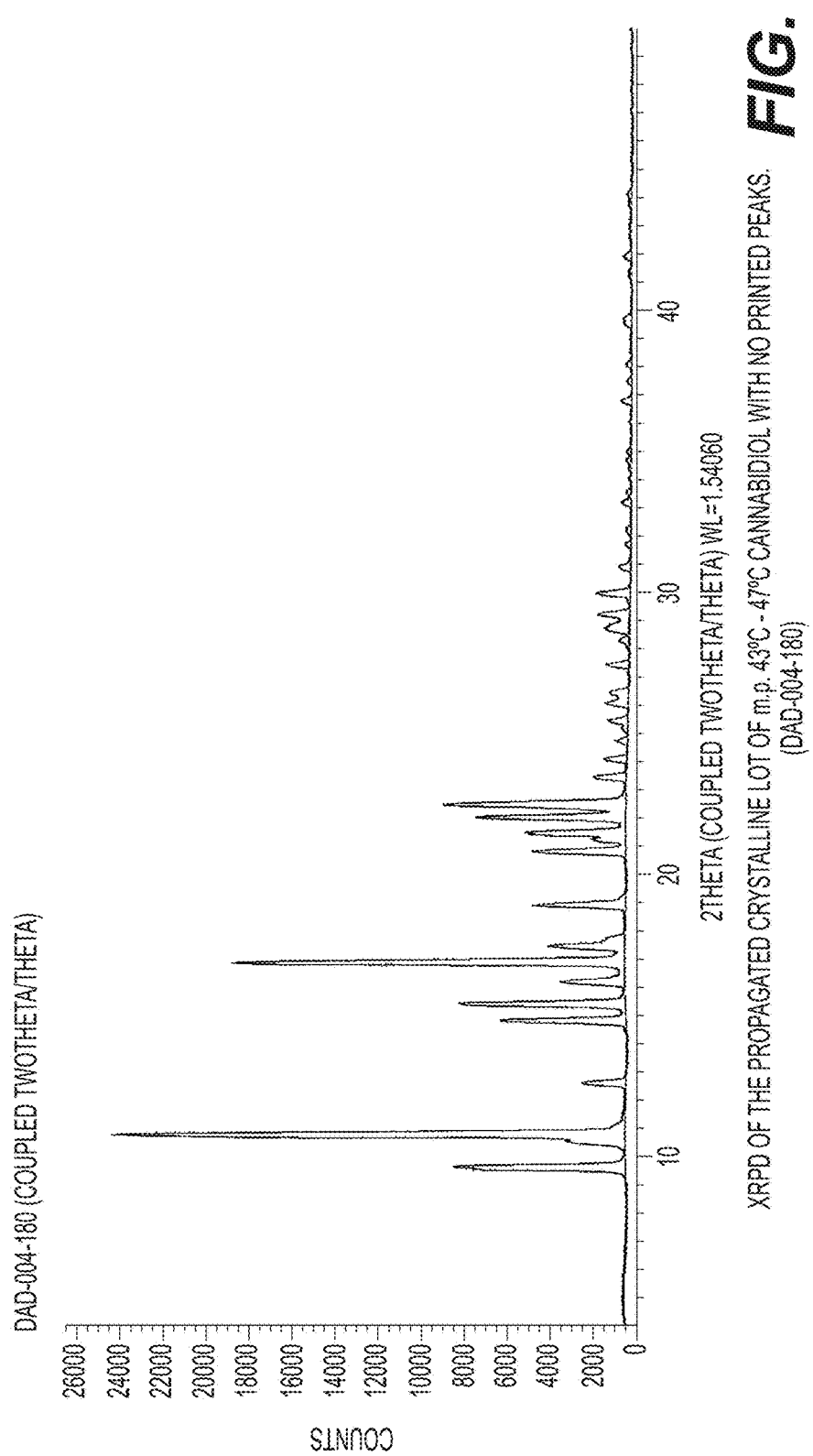
FIG. 10 is an x-ray powder diffraction pattern of the new form of (R,R)-(−)-crystalline Cannabidiol of what is described in FIG. 9.

X-ray powder diffraction patterns corresponding to the new form of (R,R)-(−)-crystalline Cannabidiol can be found in FIGS. 6, 7, 9 and 10 with FIGS. 6 and 9 being peak picked. The preparation of the sample of (R,R)-(−)-crystalline Cannabidiol for FIGS. 6 and 7 can be found at Example 6. FIGS. 9 and 10 are x-ray powder diffraction patterns corresponding to the new form of (R,R)-(−)-crystalline Cannabidiol made according to Example 5.

Example 6 illustrates a non-crystalline preparation of (R,R)-(−)-Cannabidiol, followed by seeding with crystalline Cannabidivarin to produce seeds of the new crystalline form of (R,R)-(−)-Cannabidiol. Example 5 illustrates a preparation that provided a seed crystal of (R,R)-(−)-crystalline Cannabidiol to produce additional material of the new crystalline form of (R,R)-(−)-Cannabidiol.

Seeding is a phenomenon whereby solid particles, often of the material sought to be crystallized, are added to a crystallization process to induce and influence crystallization. Seeding with the new form of crystalline Cannabidiol (such as (R,R)-(−)-crystalline Cannabidiol) may be used to help facilitate the crystallization of the new form. Seeds may also be used to form crystals from natural extracts of Cannabidiol prepared by other methods. For example, Cannabidiol extract is soluble in heptane and can be seeded with the new form of crystalline Cannabidiol to produce the new form of crystalline Cannabidiol, which then may be isolated after filtration as analogously described by Flockhart, et. al. in US 2006/0167283 A1 for Cannabidiol that melts at 66° C.-67° C. Producing the new form of crystalline Cannabidiol by seeding a plant extract comprising Cannabidiol is therefore one exemplary embodiment of the present invention.

In many embodiments of the invention, a substantially pure new form of crystalline Cannabidiol, such as (R,R)-(−)-Cannabidiol, is provided. By "substantially pure" what is meant with respect to (R,R)-(−)-Cannabidiol (either crystalline or amorphous) is (R,R)-(−)-Cannabidiol having a stereochemical purity of at least 90% wherein the amount of diastereomers of Cannabidiol, namely the (R,S) and (S,R) diastereoisomers, the (S,S)-(+)-Cannabidiol enantiomer of Cannabidiol and racemic Cannabidiol is present at less than 10% in total. In other embodiments, such stereochemical purity is at least 91%, 92%, 93%, 94%, 95%, 96%, 97%, 98%, or 99% of the (R,R)-(−)-Cannabidiol.

One embodiment of the invention includes a new form of crystalline Cannabidiol (such as crystalline (R,R)-(−)-Cannabidiol), wherein the new form has a melting point within the range of from about 37° C. to about 50° C., such as from about 39° C. to about 48° C., or from about 43° C. to about 47° C., or from about 43° C. to about 46° C.

Additional embodiments include a new form of crystalline Cannabidiol (such as crystalline (R,R)-(−)-Cannabidiol) having certain characteristics in its x-ray powder diffraction pattern. In each of FIGS. 6 and 9, the x-axis positions of the peaks in the powder x-ray diffraction patterns have been identified for different lots of the new crystal form of Cannabidiol. Tables 1-2 below list the peaks for each corresponding diffraction pattern.

TABLE 1

Figure 7:
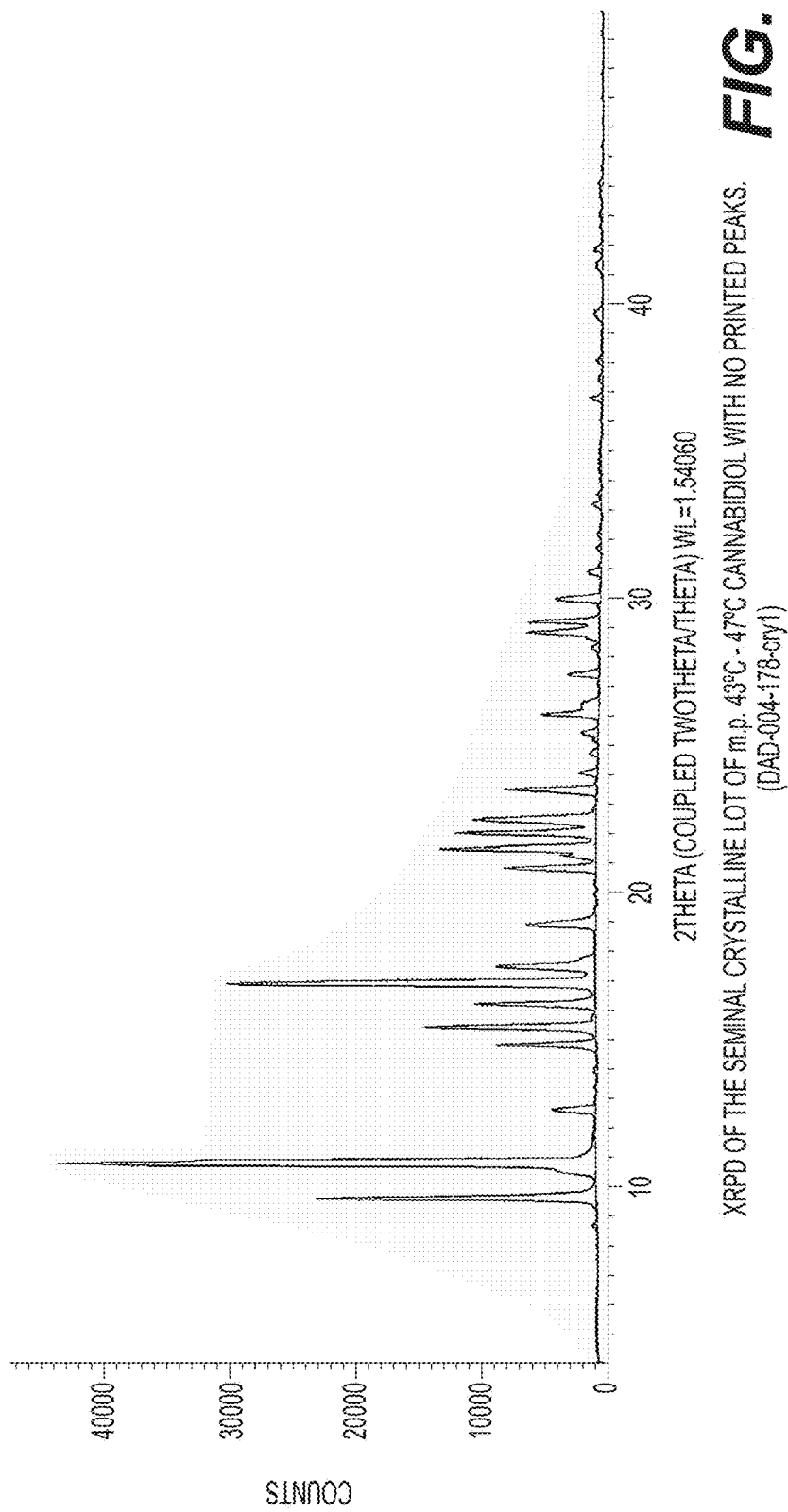
FIG. 7 is a non-peak picked x-ray powder diffraction pattern of the new form of (R,R)-(−)-crystalline Cannabidiol of what is described in FIG. 6.

XRPD Peaks for Seminal Crystalline lot of Cannabidiol (DAD-004-178-cryl), corresponding to FIGS. 6 and 7

| Index | Angle | d Value | Rel. Intensity |
| --- | --- | --- | --- |
| 0 | 8.628 | 10.24065 | 0.9% |
| 1 | 9.555 | 9.24889 | 54.3% |
| 2 | 10.512 | 8.40868 | 7.5% |
| 3 | 10.739 | 8.23170 | 100.0% |
| 4 | 12.567 | 7.03831 | 8.2% |
| 5 | 13.913 | 6.36019 | 0.5% |
| 6 | 14.795 | 5.98296 | 19.2% |
| 7 | 15.397 | 5.75015 | 32.4% |
| 8 | 16.191 | 5.46997 | 22.6% |
| 9 | 16.889 | 5.24541 | 71.0% |
| 10 | 17.453 | 5.07730 | 18.4% |
| 11 | 17.676 | 5.01365 | 3.1% |
| 12 | 18.855 | 4.70276 | 13.3% |
| 13 | 20.785 | 4.27013 | 16.8% |
| 14 | 21.234 | 4.18088 | 6.5% |
| 15 | 21.439 | 4.14140 | 26.5% |
| 16 | 21.997 | 4.03749 | 26.5% |
| 17 | 22.463 | 3.95486 | 22.7% |
| 18 | 23.495 | 3.78347 | 17.2% |
| 19 | 24.059 | 3.69597 | 3.2% |
| 20 | 24.736 | 3.59628 | 1.4% |
| 21 | 25.189 | 3.53263 | 0.9% |
| 22 | 25.416 | 3.50167 | 3.2% |
| 23 | 26.050 | 3.41787 | 10.6% |
| 24 | 26.326 | 3.38264 | 3.2% |
| 25 | 27.378 | 3.25504 | 5.8% |
| 26 | 28.286 | 3.15250 | 1.5% |
| 27 | 28.817 | 3.09561 | 13.2% |
| 28 | 29.185 | 3.05744 | 12.5% |
| 29 | 29.949 | 2.98115 | 8.1% |
| 30 | 30.877 | 2.89366 | 2.5% |
| 31 | 31.712 | 2.81933 | 0.9% |
| 32 | 32.175 | 2.77983 | 0.7% |
| 33 | 33.199 | 2.69634 | 1.9% |
| 34 | 33.539 | 2.66978 | 0.9% |
| 35 | 34.390 | 2.60565 | 0.4% |
| 36 | 36.795 | 2.44071 | 2.1% |
| 37 | 37.454 | 2.39927 | 0.7% |
| 38 | 38.083 | 2.36106 | 1.0% |
| 39 | 39.657 | 2.27091 | 1.7% |
| 40 | 41.268 | 2.18589 | 1.1% |
| 41 | 41.843 | 2.15718 | 1.1% |
| 42 | 41.898 | 2.15447 | 1.6% |

TABLE 2

XRPD Peaks for Cannabidiol that was prepared by Seeding from the material from (DAD-004-178-cryl), corresponding to FIGS. 9 and 10

| Index | Angle | d Value | Rel. Intensity |
| --- | --- | --- | --- |
| 0 | 9.563 | 9.24119 | 33.4% |
| 1 | 10.501 | 8.41775 | 11.6% |
| 2 | 10.729 | 8.23953 | 100.0% |
| 3 | 12.551 | 7.04673 | 8.7% |
| 4 | 14.785 | 5.98679 | 24.3% |
| 5 | 15.385 | 5.75458 | 32.1% |
| 6 | 16.165 | 5.47883 | 12.5% |
| 7 | 16.869 | 5.25147 | 76.2% |
| 8 | 17.427 | 5.08474 | 14.6% |
| 9 | 17.679 | 5.01273 | 3.6% |
| 10 | 18.856 | 4.70240 | 17.8% |
| 11 | 19.068 | 4.65068 | 1.5% |
| 12 | 20.769 | 4.27345 | 18.4% |
| 13 | 21.197 | 4.18810 | 6.2% |
| 14 | 21.421 | 4.14488 | 19.2% |
| 15 | 21.993 | 4.03835 | 29.3% |
| 16 | 22.452 | 3.95676 | 35.4% |
| 17 | 23.420 | 3.79543 | 6.4% |
| 18 | 24.059 | 3.69606 | 4.6% |
| 19 | 24.708 | 3.60042 | 1.9% |
| 20 | 25.175 | 3.53456 | 1.2% |
| 21 | 25.417 | 3.50152 | 3.7% |
| 22 | 26.037 | 3.41950 | 4.1% |
| 23 | 26.417 | 3.37116 | 3.5% |
| 24 | 27.387 | 3.25400 | 4.4% |
| 25 | 28.261 | 3.15529 | 2.0% |
| 26 | 28.689 | 3.10920 | 4.9% |
| 27 | 29.187 | 3.05723 | 6.3% |
| 28 | 29.941 | 2.98194 | 6.6% |
| 29 | 30.874 | 2.89390 | 2.3% |
| 30 | 31.677 | 2.82240 | 1.1% |
| 31 | 32.209 | 2.77694 | 1.0% |
| 32 | 33.173 | 2.69840 | 1.8% |
| 33 | 33.552 | 2.66884 | 0.7% |
| 34 | 34.688 | 2.58399 | 0.9% |
| 35 | 34.981 | 2.56297 | 0.9% |
| 36 | 36.046 | 2.48966 | 0.6% |
| 37 | 36.759 | 2.44297 | 2.0% |
| 38 | 37.471 | 2.39822 | 0.9% |
| 39 | 38.064 | 2.36219 | 1.2% |
| 40 | 38.584 | 2.33156 | 0.3% |
| 41 | 39.563 | 2.27607 | 1.4% |
| 42 | 39.657 | 2.27087 | 1.6% |
| 43 | 41.904 | 2.15416 | 1.6% |

In many embodiments of the invention, the new form of crystalline Cannabidiol (such as (R,R)-(−)-crystalline Cannabidiol) may be characterized by one or more of the peaks set forth in FIGS. 6,7,9, and 10.

For example, a peak at about 10.7° 2θ in the powder x-ray diffraction pattern may be used to characterize the new form. Another embodiment therefore includes a new form of crystalline Cannabidiol (such as crystalline (R,R)-(-)-Cannabidiol) having a powder x-ray diffraction pattern comprising a peak at about 10.7° 2θ, such as for crystalline Cannabidiol having a melting point within the ranges of from about 37° C. to about 50° C., such as from about 39° C. to about 48° C., or from about 43° C. to about 47° C., or from about 43° C. to about 46° C.

In Table 1, there is a peak at about 10.74° 2θ, in Table 2 the corresponding peak is at about 10.73° 2θ. Averaging these values yields a peak at about 10.735° 2θ, which can be rounded to 10.7° 2θ. These values are indicative of variability that may be present in their measurements.

In other embodiments, more than one peak may be used to characterize the new form of crystalline Cannabidiol. For example, in some embodiments the new form has a powder x-ray diffraction pattern comprising a peak at about 10.7° 2θ, at about 14.8° 2θ, at about 21.4° 2θ, at about 29.9° 2θ, at about 21.2° 2θ, or at several or all of these positions. In some embodiments, the new form has a powder x-ray diffraction pattern comprising a peak at about 10.7° 2θ and at about 14.8° 2θ. In further embodiments, the new form has a powder x-ray diffraction pattern comprising a peak at each of the following positions: about 10.7° 2θ, about 14.8° 2θ and about 21.4° 2θ. In further embodiments the new form alternatively or additionally has a powder x-ray diffraction pattern comprising a peak at about 21.2° 2θ and at about 29.9° 2θ.

Other peaks in the x-ray powder diffraction pattern of the new form may also be used to characterize this crystalline form. For example, one or more peaks at about 9.6° 2θ, 10.5° 2θ, or 23.4° 2θ may be used to characterize the new form of (R,R)-(-)-crystalline Cannabidiol. In other embodiments, one or more peaks at about 14.8° 2θ, 21.2° 2θ, 21.4° 2θ, 26.0° 2θ, or 27.4° 2θ, may be used to characterize the new form.

In another embodiment, a diffraction pattern substantially the same as any one of FIGS. 6, 7 9 and 10 may be used to characterize the new form of (R,R)-(-)-crystalline Cannabidiol.

The X-ray coordinates for crystalline Cannabidiol, m.p. 66° C.-67° C., are listed in the publication [*Acta Cryst.* (1977) B33, P3211-3214], the Cambridge Crystallographic Database, and have been published by the National Bureau of Standards [National Bureau of Standards (U.S.), Monogr. 25 Sec 16, pp. 111-113, Library of Congress Catalog Card Number: 53-61386] FIG C. An XRPD pattern was calculated and plotted based on this Cambridge Crystallographic Database data for Cannabidiol having m.p. 66° C.-67° C. The calculated XRPD pattern (peak height and position) generated from the published single crystal solution data for the Cannabidiol with m.p. 66° C.-67° C. is shown in Table 3 below.

TABLE 3

Calculated Table of XRPD peaks from Acta Cryst. (1977). B33, 3211-3214, corresponding to FIG. 11

| Cannabidiol 2-Theta ° | d. A | I/Io, % |
|---|---|---|
| 5.14 | 17.18 | 2 |
| 8.37 | 10.55 | 5 |
| 9.42 | 9.38 | 33.6 |
| 9.78 | 9.04 | 100 |

TABLE 3-continued

Calculated Table of XRPD peaks from Acta Cryst. (1977). B33, 3211-3214, corresponding to FIG. 11

| Cannabidiol 2-Theta ° | d. A | I/Io, % |
|---|---|---|
| 10.28 | 8.6 | 37.8 |
| 11.79 | 7.5 | 40.6 |
| 12.56 | 7.04 | 28 |
| 13.2 | 6.7 | 45.4 |
| 13.87 | 6.38 | 32.5 |
| 15.16 | 5.84 | 35.1 |
| 16.19 | 5.47 | 5.7 |
| 16.65 | 5.32 | 11 |
| 17.44 | 5.08 | 74.5 |
| 18.01 | 4.92 | 20.7 |
| 18.9 | 4.69 | 76.6 |
| 19.58 | 4.53 | 28.3 |
| 20.66 | 4.3 | 56.3 |
| 21.75 | 4.08 | 67.2 |
| 22.24 | 3.99 | 88 |
| 22.79 | 3.9 | 46.5 |
| 23.86 | 3.73 | 30.7 |
| 24.55 | 3.62 | 24.4 |
| 25.43 | 3.5 | 24.2 |
| 26.79 | 3.32 | 15.2 |
| 27.76 | 3.21 | 21.1 |
| 28.78 | 3.1 | 18.9 |
| 29.22 | 3.05 | 32.3 |
| 30.55 | 2.92 | 7.3 |
| 32.28 | 2.86 | 16.4 |
| 32.73 | 2.73 | 10.3 |
| 33.46 | 2.68 | 13.1 |
| 34.21 | 2.62 | 15.8 |
| 34.74 | 2.58 | 21.2 |
| 35.93 | 2.5 | 7.6 |
| 36.72 | 2.45 | 10.2 |
| 37.92 | 2.37 | 9.9 |
| 38.29 | 2.35 | 8.8 |
| 39.56 | 2.28 | 7.4 |

Figure 1B:
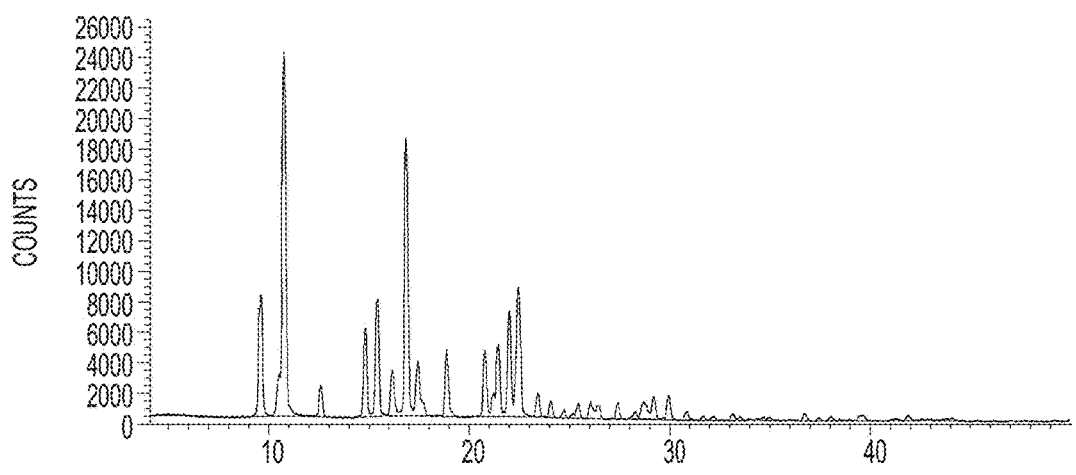
FIG. 1B is an XRPD pattern of the new form according to an embodiment of the invention (from FIG. 10).
Figure 3:
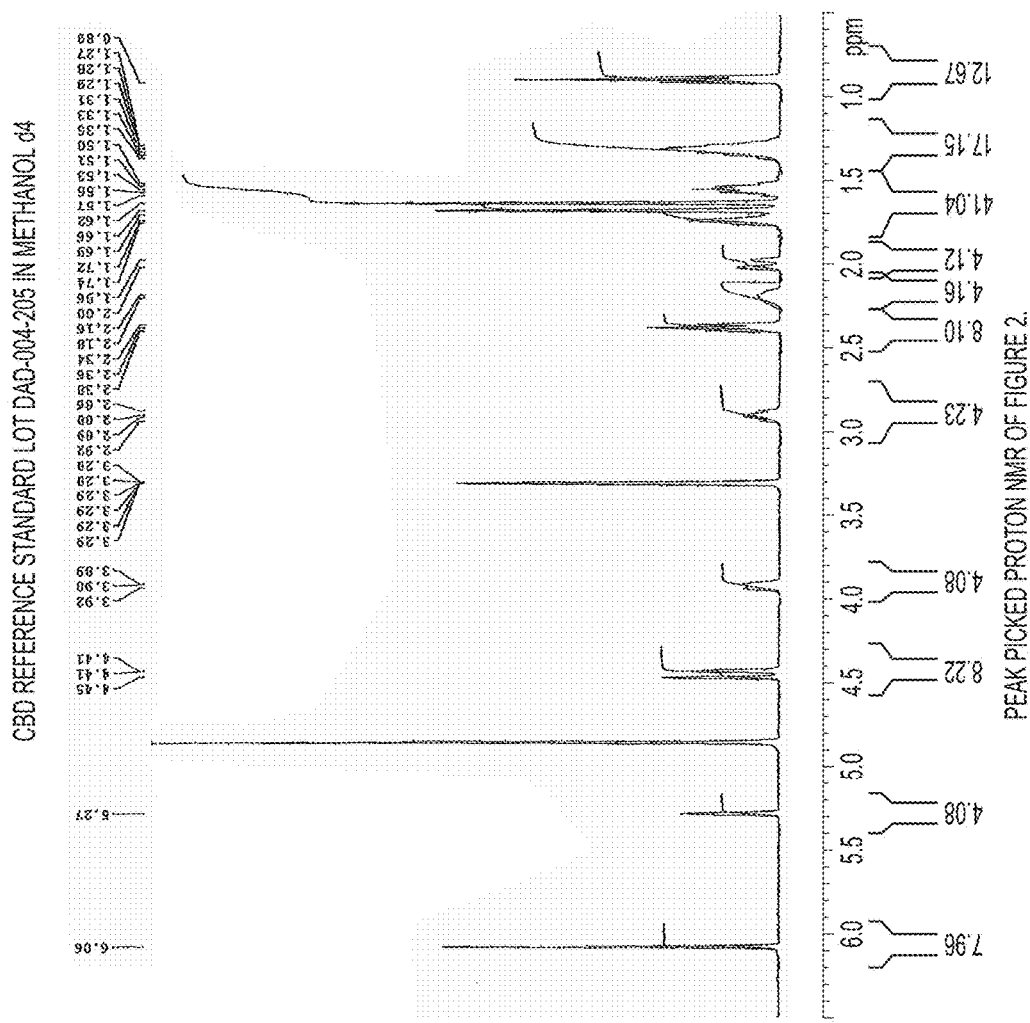
FIG. 3 is a peak-picked $^1$H-NMR spectrum of a solution of the new form of (R,R)-(−)-Cannabidiol in $d_4$ methanol.
Figure 4:
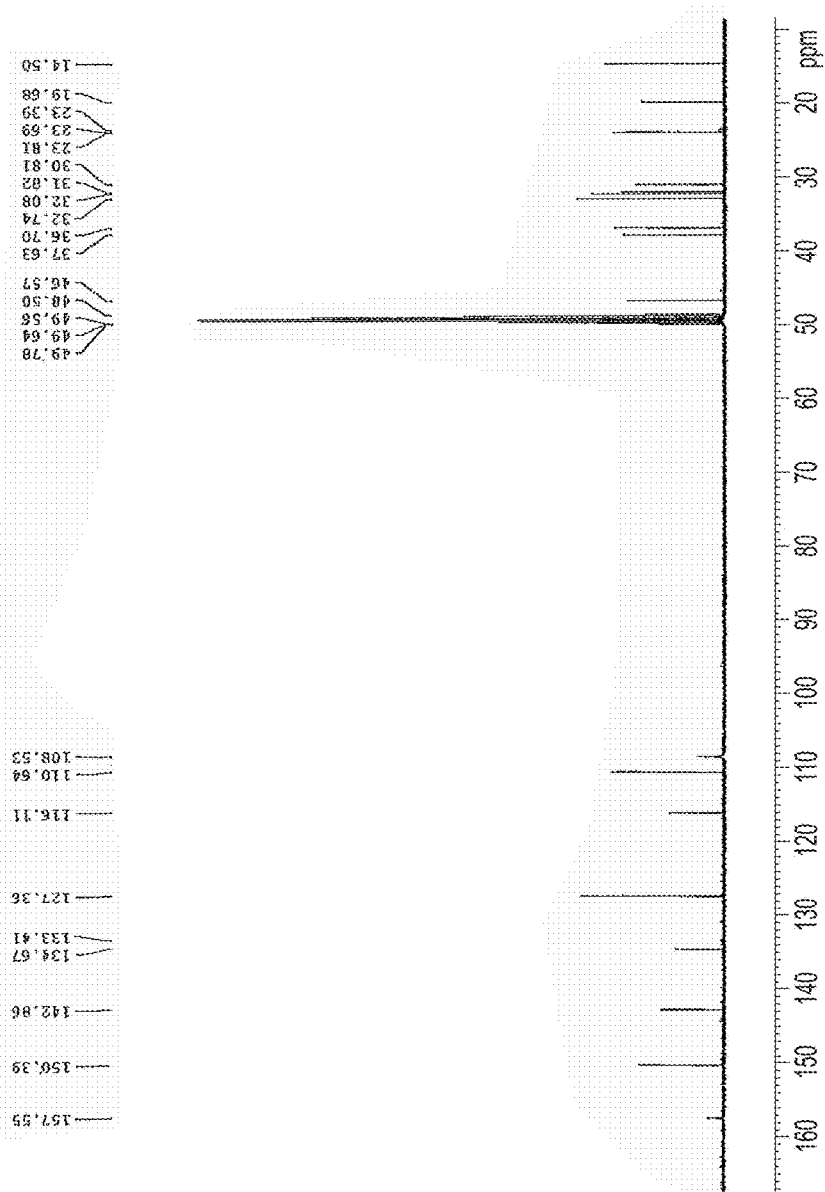
FIG. 4 is a peak-picked $^{13}$C-NMR spectrum of a solution of the new form of (R,R)-(−)-Cannabidiol in $d_4$ methanol.
Figure 11:
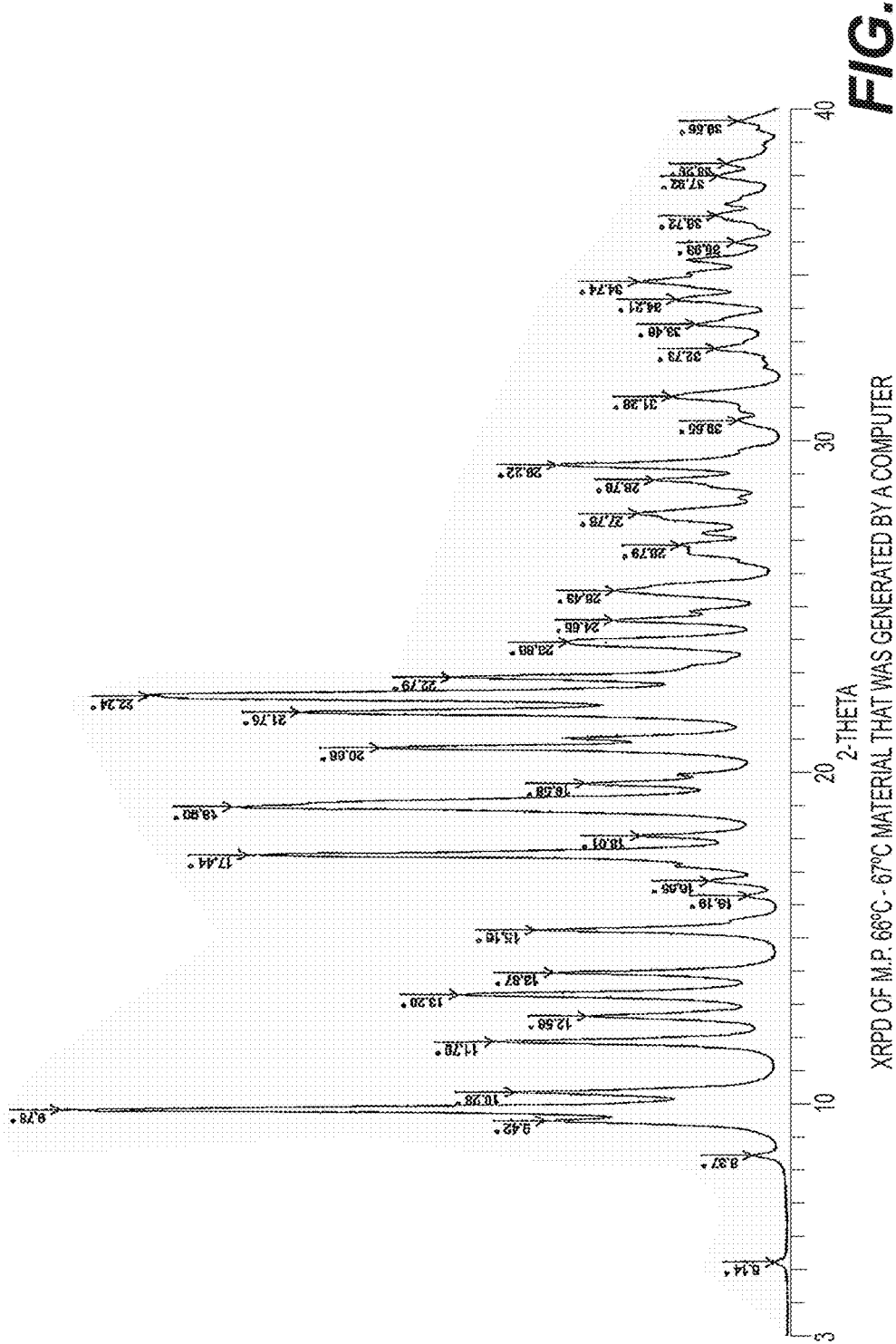
FIG. 11 is a large scale printout of a computer generated XRPD pattern of a form of Cannabidiol that melts at 66° C.-67° C. that was generated from the data found in the publication by Jones, Peter G; et. al.: *Acta Cryst.* (1977) B33, P3211-3214.

The corresponding generated XRPD plot for Cannabidiol with m.p. 66° C.-67° C. is shown in FIGS. 1 and 11. The data confirms that the crystalline form of the invention is a new form compared to the form having a melting point of 66° C.-67° C.

In further embodiments of the invention, the new form of crystalline Cannabidiol (such as crystalline (R,R)-(-)-Cannabidiol), has a powder x-ray diffraction pattern that does not comprise a peak at one or more of the following positions: about 8.4° 2θ, about 9.8° 2θ, about 11.8° 2θ, about 13.2° 274 , about 13.9° 2θ, about 18.0° 2θ, about 19.6° 2θ, about 22.8° 2θ, about 24.6° 2θ and about 25.4° 2θ.

Figure 5:
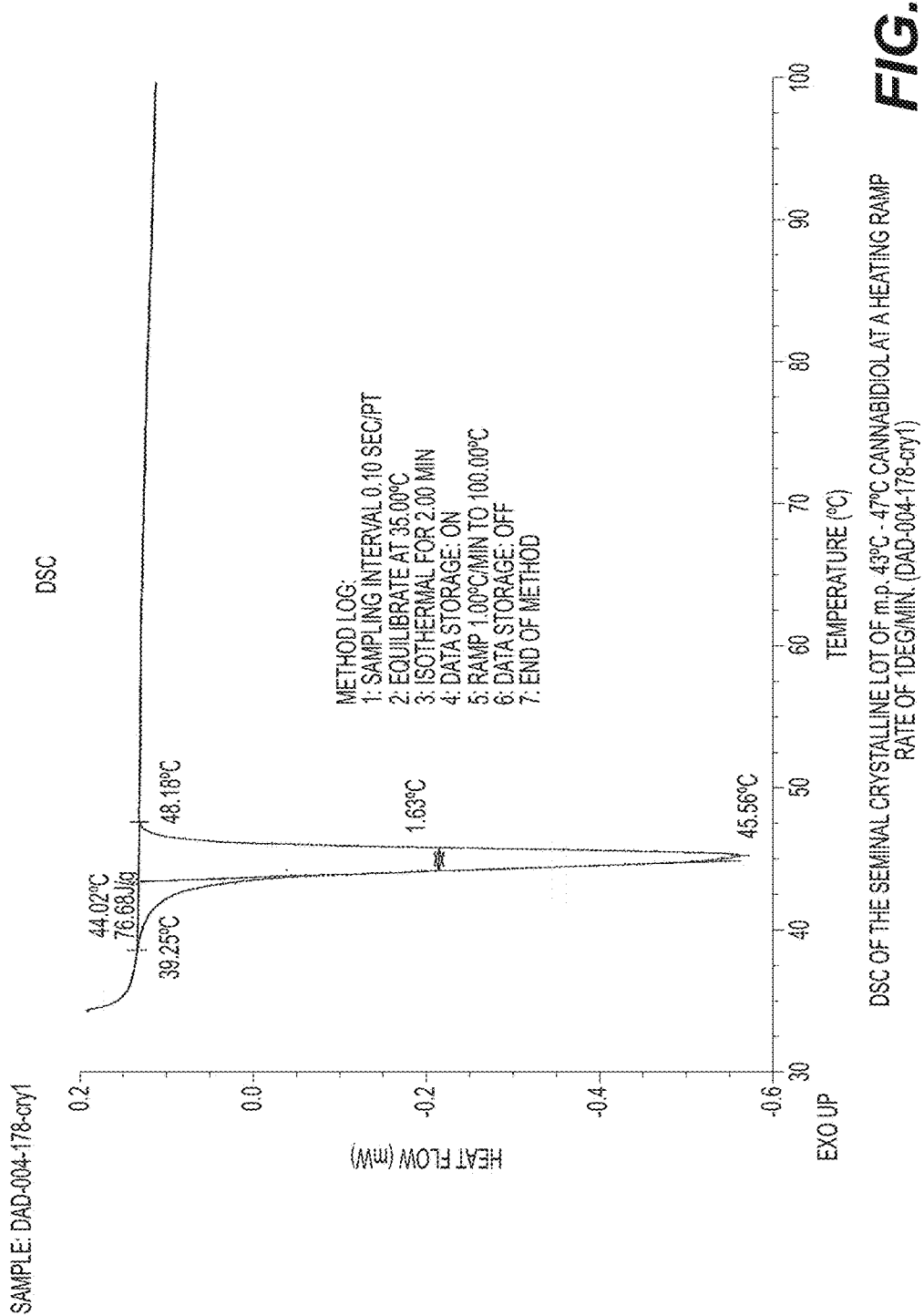
FIG. 5 is a differential scanning calorimetry thermogram of the new form of (R,R)-(−)-crystalline Cannabidiol, which was prepared by seeding with Cannabidivarin.
Figure 8:
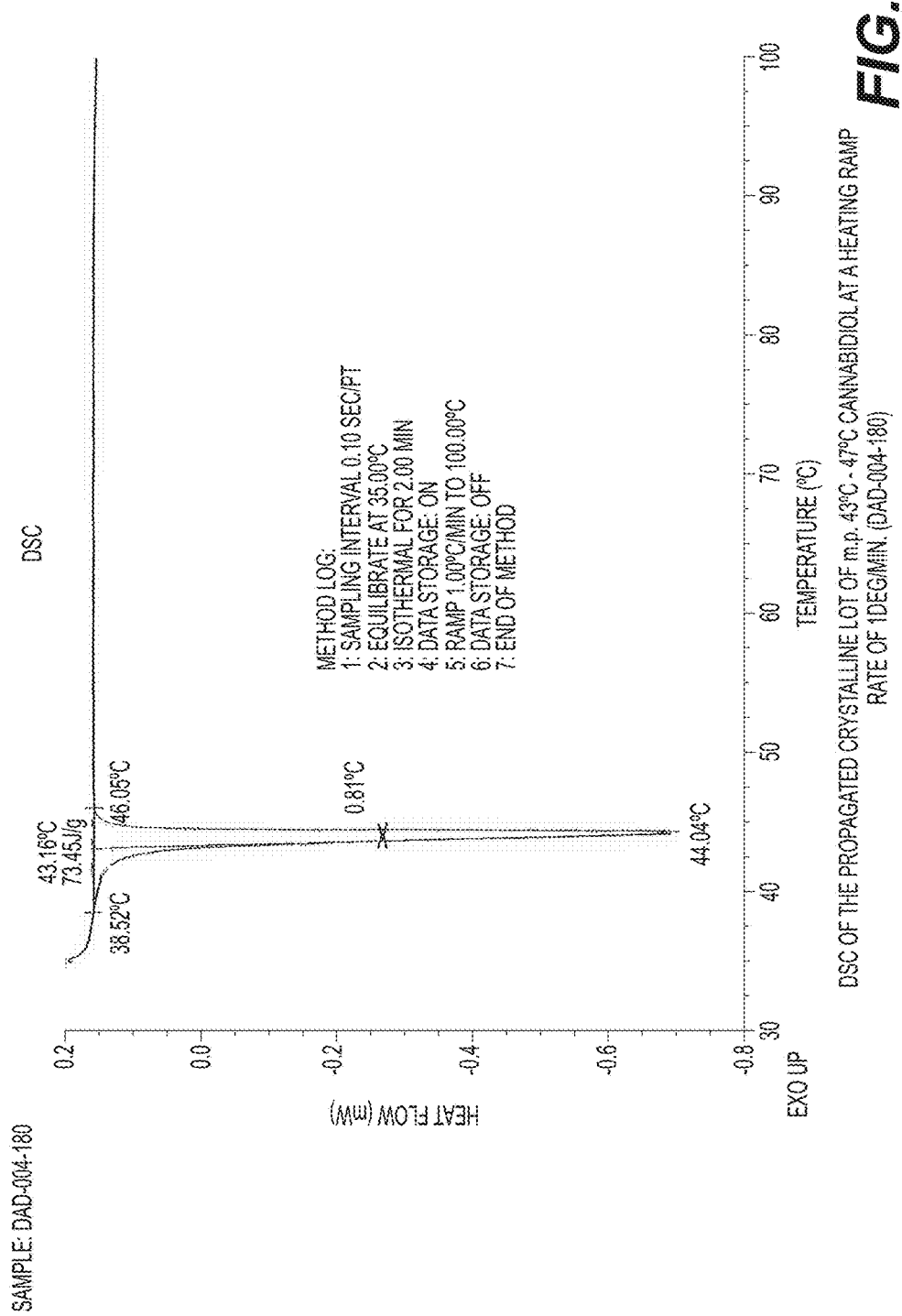
FIG. 8 is a differential scanning calorimetry thermogram of the new form of (R,R)-(−)-crystalline Cannabidiol of a different lot prepared by seeding with Cannabidiol.
Figure 12:
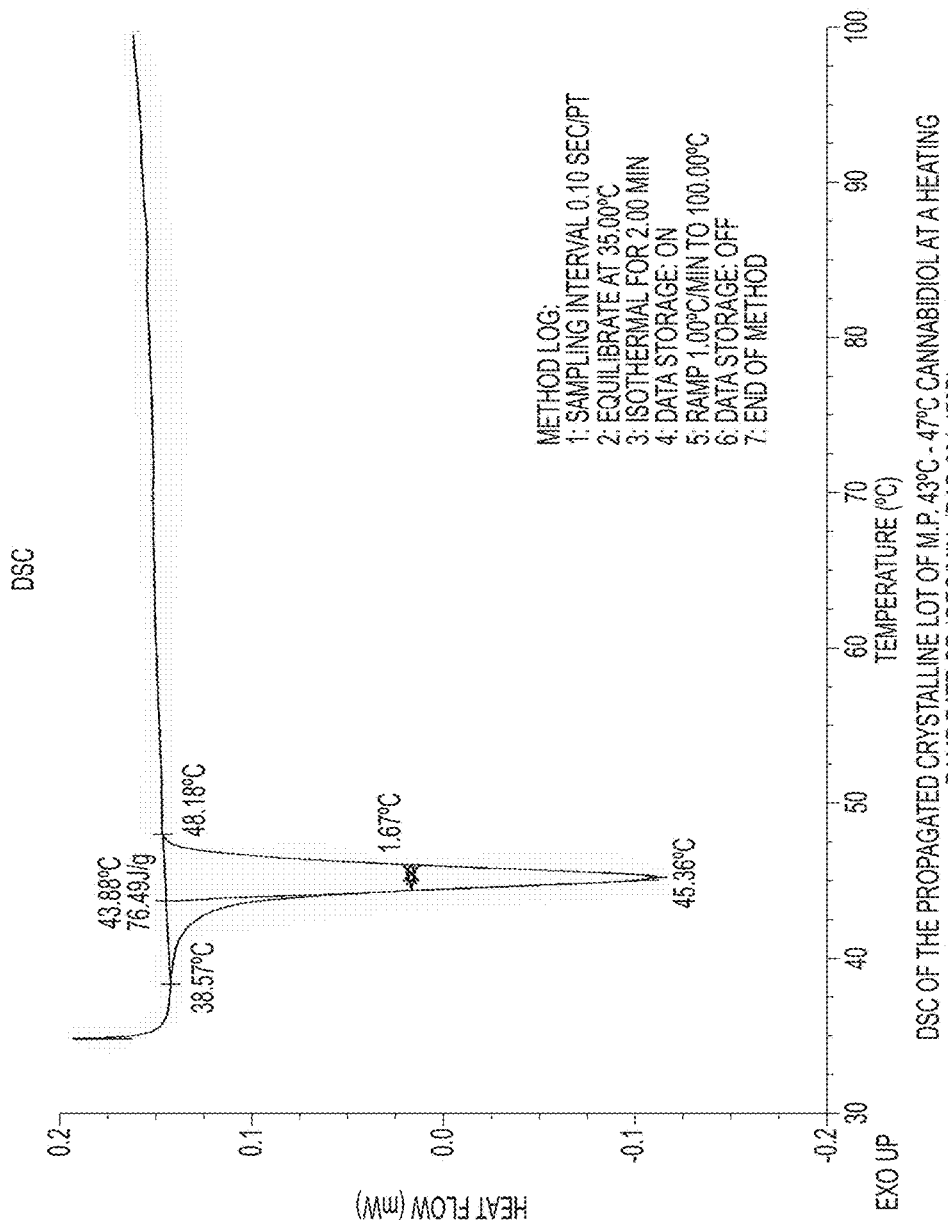
FIG. 12 is a differential scanning calorimetry thermogram of the new form of (R,R)-(−)-crystalline Cannabidiol prepared by seeding with Cannabidiol.

Thermal methods may also be used to characterize the new form of crystalline Cannabidiol alone or in conjunction with other analytical techniques. FIG. 5 is a differential scanning calorimetry thermogram of the new form of (R,R)-(-)-crystalline Cannabidiol prepared by Example 6. FIG. 8 is a differential scanning calorimetry thermogram of the new form of (R,R)-(-)-crystalline Cannabidiol prepared by Example 5. FIG. 12 is a differential scanning calorimetry thermogram of another lot of the new form of (R,R)-(-)-crystalline Cannabidiol.

In each thermogram at above 35° C., a single endotherm is present, consistent with the melt of a crystalline solid. In FIGS. 5,8 and 12, a temperature ramp rate of 1° C. per minute was used starting at 35° C. all the way to 100° C. The peak maxima were recorded at about 44° C. and 46° C. respectively. Thus, a peak maximum in a DSC thermogram endotherm at from about 43° C. to 47° C., such as from about 43° C. to about 45° C. may also be used to characterize the new form of crystalline Cannabidiol, such as (R,R)-(-)-crystalline Cannabidiol.

In other embodiments, the thermal characterizing data such as an endotherm onset, maximum, or both together, may be used with one or more x-ray diffraction peaks for the new form disclosed previously to characterize the new form of crystalline Cannabidiol, such as (R,R)-(−)-crystalline Cannabidiol. Thus, for example, an endotherm maximum at from about 43° C. to about 47° C., or from about 43° C. to about 45° C., together with an x-ray powder diffraction peak at about 10.7° 2θ, at about 14.8° 2θ, at about 21.4° 2θ, at about 29.9° 2θ, at about 21.2° 2θ, or at several or all of these positions, may be used to characterize the new form of crystalline Cannabidiol.

Two synthetic and crystallization routes are disclosed herein in Examples 5 and 6 respectively for making the new form of crystalline Cannabidiol. Each describes making the new form, including (R,R)-(−)-crystalline Cannabidiol, having a melting temperature at about 43° C.-47° C. Additionally, Example 5 describes another synthetic route for making the new form of (R,R)-(−)-crystalline Cannabidiol. A melting point was observed for each crystalline Example ranging from about 43° C.-47° C. for Example 5, about 45.6° C., 44.0° C. for Examples 6 and 5, respectively. Thus, a melting point temperature of between about 43° C. and 47° C., for example, may be used to characterize the new form of crystalline Cannabidiol, such as (R,R)-(−)-crystalline Cannabidiol. Melting point may be used alone or together with one or more analytical techniques to characterize the new form of crystalline Cannabidiol. For example, a melting point of, for example, from about 43° C. to about 47° C. together with one or more peaks at about 9.6° 2θ, 10.5° 2θ, 10.7° 2θ, 14.8° 2θ, 21.2° 2θ, or 23.4° 2θ may be used to characterize the new form. Thus, for example, a melting point within the range of from about 43° C. and 47° C. together with an x-ray powder diffraction peak at about 10.7° 2θ, at about 14.8° 2θ, at about 21.4° 2θ, at about 29.9° 2θ, at about 21.2° 2θ, or at several or all of these positions, may be used to characterize the new form.

Figure 13:
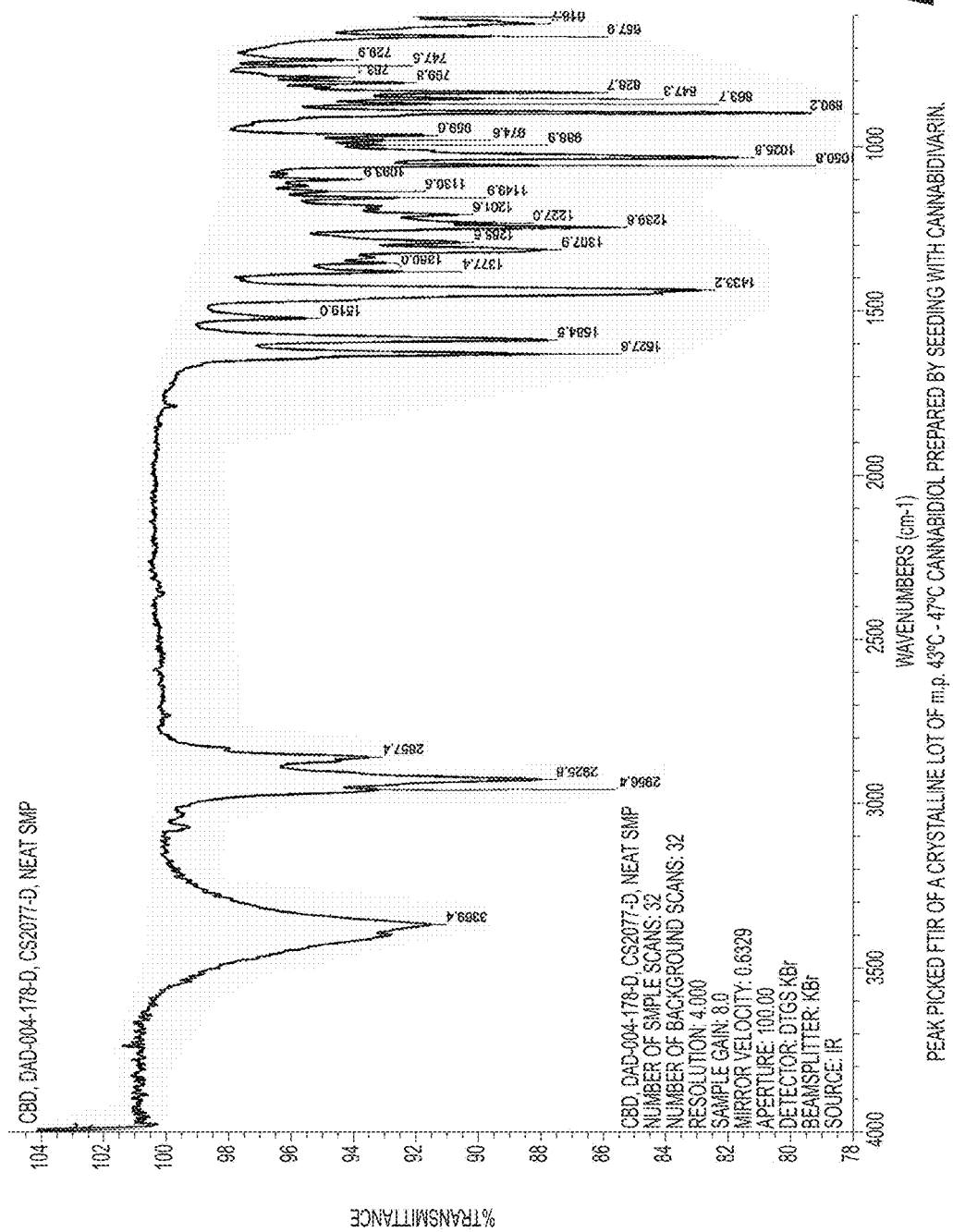
FIG. 13 is a peak-picked FT-IR spectrum of the new form of (R,R)-(−)-crystalline Cannabidiol.
Figure 14:
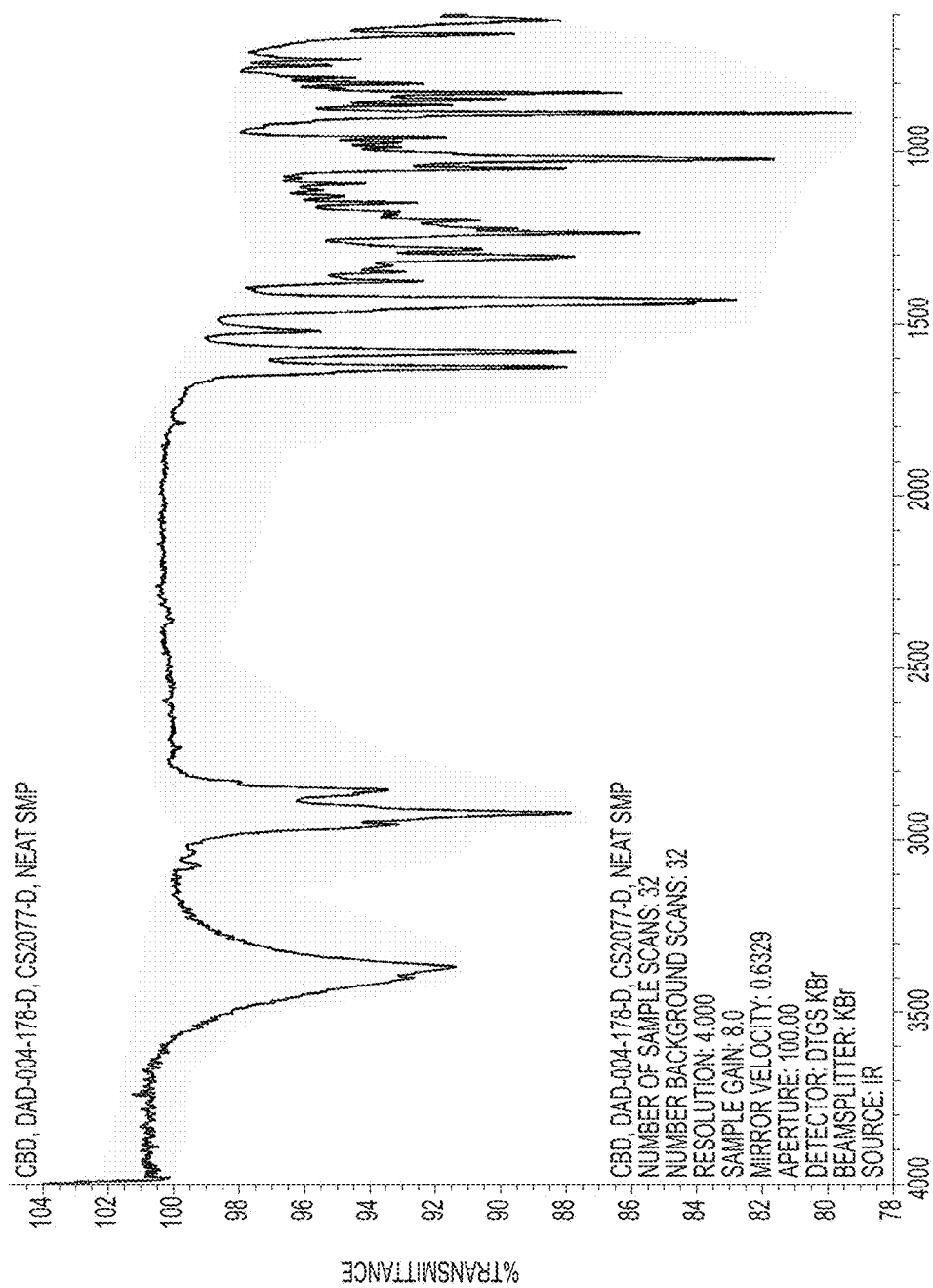
FIG. 14 is a non-peak-picked FT-IR spectrum of the new form of (R,R)-(−)-crystalline Cannabidiol shown in FIG. 13.

Turning to FIG. 13, for example, an FT-IR spectrum having one or more peaks at about 658 cm$^{-1}$, 890 cm$^{-1}$, 1026 cm$^{-1}$, 1433 cm$^{-1}$, 1585 cm$^{-1}$, 1628 cm$^{-1}$ 2926 cm$^{-1}$ may also be used to characterize the new form of crystalline Cannabidiol. In other embodiments, such one or more FT-IR peaks may be used together with one or more peaks in the x-ray powder diffraction pattern of crystalline Cannabidiol such as at about 10.7° 2θ, at about 14.8° 2θ, at about 21.4° 2θ, at about 29.9° 2θ, at about 21.2° 2θ, or at several or all of these positions to characterize the new form. In still other embodiments, one or more of said FT-IR peaks together with one or more of said x-ray powder diffraction peaks together with a melting point within the range of about 43° C. to about 47° C. may be used to characterize the new form. In addition to the melting point, or in place thereof, one may also include a DSC maximum endotherm of from about 43° C. to about 47° C., or from about 43° C. to about 45° C., to characterize crystalline Cannabidiol. Thus, for example, a melting point within the range of from about 43° C. to about 47° C. and a peak in the FT-IR spectrum of about 1585 cm$^{-1}$ may be used to characterize the new form of (R,R)-(−)-crystalline Cannabidiol. Further, the FT-IR peaks disclosed herein may be used in combination with both x-ray diffraction data and thermal data set forth herein to characterize the new form of (R,R)-(−)-crystalline Cannabidiol. Thus, for example an FT-IR peak at about 1628 cm$^{-1}$, together with a DSC maximum endotherm at from about 43° C. to about 47° C., together with an x-ray powder diffraction peak at about 10.7° 2θ may be used to characterize the new form of (R,R)-(−)-crystalline Cannabidiol.

An exemplary process for preparing (R,R)-(−)-Cannabidiol is set forth below, and the (R,R)-(−)-Cannabidiol may then be crystallized according to the Examples to produce the new crystalline form of (R,R)-(−)-Cannabidiol:

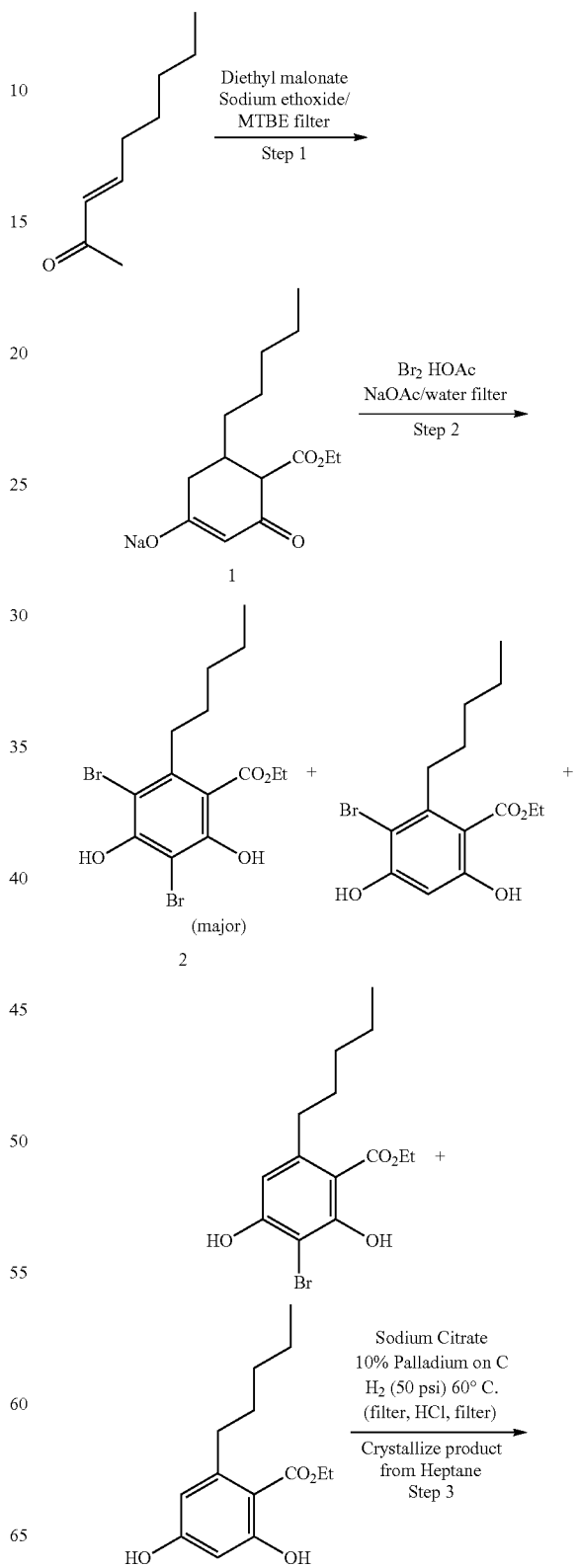

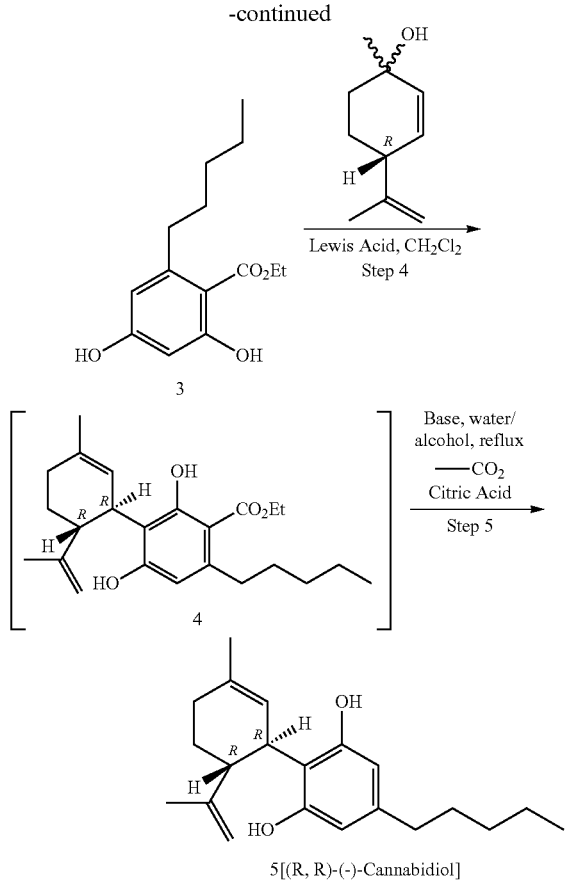

5[(R, R)-(-)-Cannabidiol]

Note that although the major stereoisomers are depicted in this reaction scheme, these may be accompanied by other minor stereoisomeric by-products giving a small amount of the S,S-enantiomer and small amounts of the R,S and S,R diastereoisomers of the intermediate 4 as well as the possibility of trace amounts of the corresponding stereoisomers in the product 5.

A process for preparing compound 1 can be found in Example 2. A process for preparing compound 2 can be found in Example 3. A process for preparing compound 3 can be found in Example 4. A process for preparing compound 5 via intermediate 4 can be found in Examples 5 and 6.

Tables 1 and 2 presented earlier are the peak lists corresponding to FIGS. 6 and 7) and (9 and 10) respectively.

In preparing the new form of (R,R)-(−)-crystalline Cannabidiol or substantially pure forms thereof, synthetically-prepared Cannabidiol, can be dissolved in a suitable solvent. A suitable solvent is a solvent in which (R,R)-(−)-crystalline Cannabidiol dissolves such as methyl tert-butyl ether (MTBE). Crystallization may occur by adding an anti-solvent, such as heptane, where crystalline Cannabidiol has more limited solubility. By removing MTBE such as by vacuum, the crystalline Cannabidiol may become concentrated in heptane. Reducing the temperature in the presence of seed crystals of the new form, whose preparation in the presence of Cannabidivarin, m.p. 116° C.-120° C., is listed in Example 6, and whose propagation is listed in Example 5, without Cannabidivarin seeding, may then cause crystalline Cannabidiol, such as the new form of (R,R)-(−)-crystalline Cannabidiol as the case may be, to form.

The process of making the new form of (R,R)-(−)-crystalline Cannabidiol described in Example 6 utilizes seed crystals of Cannabidivarin. Such seed crystals may be crystalline Cannabidivarin as described in co-pending U.S. Provisional Application No. 62/344,005 titled "Crystalline Cannabidivarin," filed on Jun. 1, 2016, the entire contents of which are specifically incorporated by reference herein.

In view of the above, an additional embodiment of the invention is a process for making the new form of crystalline Cannabidiol (such as (R,R)-(−)-crystalline Cannabidiol), which comprises:
  providing a solution of Cannabidiol in a suitable solvent;
  contacting the solution of Cannabidiol with an antisolvent to form a mixture; and
  removing the suitable solvent from the mixture in the presence of seed crystals under conditions sufficient to make the crystalline Cannabidiol.

The seed crystals in such a process may, for example, be crystalline Cannabidiol, such as (R,R)-(−)-crystalline Cannabidiol. Such seed crystals may have any characteristics of the new form described previously herein, such as a melting point within the range of from about 43° C. to about 47° C., and/or a powder x-ray diffraction pattern comprising a peak at about 10.7° 2θ, at about 14.8° 2θ, at about 21.4° 2θ, at about 29.9° 2θ, at about 21.2° 2θ, or at several or all of these positions.

The seed crystals in the process may alternatively, for example, be crystalline Cannabidivarin, such as (R,R)-(−)-crystalline Cannabidivarin described above. For example, the crystalline Cannabidivarin seed crystals may have a powder x-ray diffraction pattern comprising a peak at one or more of the following positions: about 9.4° 2θ, about 11.7° 2θ, about 14.4° 2θ, about 15.5° 2θ, and about 17.1° 2θ.

Solid Cannabidiol such as the new form of (R,R)-(−)-crystalline Cannabidiol, which may include substantially pure forms thereof, may be prepared with various different particle size distributions. The particles may be prepared from the synthetic preparations and particle size may be further engineered by micronization or milling. Precipitation rate may also affect particle size. Examples of such distributions ($D_{90}$) include between about 5 to 200 microns including values and ranges in between such as about 100 to 200 microns, about 50 to 100 microns, about 30 to 50 microns, about 20 to 30 microns, and about 5 to 20 microns. All particle size distributions herein are given as $D_{90}$ values.

Other embodiments herein provide pharmaceutical compositions or formulations comprising the new form of crystalline Cannabidiol, such as (R,R)-(−)-crystalline Cannabidiol, which may include substantially pure forms thereof, as described herein and which may include one or more pharmaceutically acceptable excipients. Methods for preparing such formulations or compositions are provided herein.

Compositions or formulations are formulated, dosed, and administered in a fashion consistent with good medical practice. Factors for consideration in this context include the particular medical disorder being treated, the particular patient being treated, the clinical condition of the individual patient, the cause of the disorder, the site of delivery of the agent, the method of administration, the scheduling of administration, and other factors known to medical practitioners.

Solid Cannabidiol, such as the new form of crystalline Cannabidiol, which may include substantially pure forms thereof, can be formulated to be administered by any suitable means, including oral, topical (including buccal and sublingual), rectal (e.g., suppositories), vaginal, transdermal, parenteral, subcutaneous, intraperitoneal, intrapulmonary, intradermal, intrathecal and epidural and intranasal (such as nasal sprays), and, if desired for local treatment, intralesional administration. Parenteral infusions include intramuscular, intravenous, intraarterial, intraperitoneal, or subcutaneous administration.

Solid Cannabidiol, such as the new form of crystalline Cannabidiol, which may include substantially pure forms thereof, can be administered in any convenient administrative form (e.g., tablets, gel caps, powders, capsules, solutions, dispersions, suspensions, liposomes, microsomes, syrups, sprays, suppositories, gels, emulsions, patches.) Such compositions can contain components conventional in pharmaceutical preparations (e.g., diluents, carriers, pH modifiers, preservatives, solubilizers, stabilizers, wetting agents, emulsifiers, sweeteners, colorants, flavorants, salts for varying the osmotic pressure, buffers, masking agents, antioxidants.) They can also contain still other therapeutically active substances. Such formulations may also be delivered in liquid form where the Cannabidiol has been sourced as a solid such as a crystalline solid. Such liquid forms include oral liquid dosage forms including liquid solutions, liquid emulsions, solid-liquid emulsions, for example. The formulations may be prepared so as to be sustained release, extended release, or as a prodrug to promote extended release.

An example formulation is prepared by mixing the crystalline new form of Cannabidiol, such as (R,R)-(−)-crystalline Cannabidiol, which may include substantially pure (R,R)-(−)-crystalline Cannabidiol as described and claimed herein and a pharmaceutically acceptable excipient. Suitable excipients are well known to those skilled in the art and are described in detail in, e.g., Allen L.V. et al., Ansel's Pharmaceutical Dosage Forms and Drug Delivery Systems (2005) Lippincott, Williams & Wilkins; Allen L.V. et al., Remington: The Science and Practice of Pharmacy (2012) Pharmaceutical Press; and Rowe R. C, Handbook of Pharmaceutical Excipients (2006) Pharmaceutical Press. Once formulated, the solid Cannabidiol may be retained in solid, such as in crystalline form. Alternatively, the solid Cannabidiol may be changed into a non-solid form, such as a liquid form, in the formulation.

The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives.

The dosages at which solid Cannabidiol, such as the new form of crystalline Cannabidiol, which may include substantially pure forms thereof, may be administered can vary within wide limits and will, of course, be fitted to the individual requirements in each particular case. In some embodiments, in the case of oral administration, a daily dosage of about 0.01 to 1000 mg per kg of solid Cannabidiol, such as the new form of crystalline Cannabidiol, which may include substantially pure forms thereof, may be appropriate. In a clinical trial utilizing non-synthetically-prepared Cannabidiol for the treatment of focal seizures, the formulated product, known as GWP42006, was dosed twice per day at 400 mg each (Clinicaltrials.gov Identifier NCT02369741) in the treatment portion of the study. Other dosages include 5 mg/kg/day and 25 mg/kg/day and values in such as about 6, 7, 8, 9, 10, 11, 12, 13, 14, 15, 16, 17, 18, 19, 20, 21, 22, 23, and 24 mg/kg/day.

The new form of crystalline Cannabidiol, such as (R,R)-(−)-crystalline Cannabidiol, can be effective in a variety of treatments. For example, the new form can be administered in methods of treating epilepsy, cancer, pain or inflammation. The new form could also be administered simultaneously or sequentially with a pharmaceutically effective amount of another active agent useful for any one of these treatments. As an example, one embodiment includes a method of treating cancer comprising administering to a patient in need of the treatment a pharmaceutically effective amount of the new form of crystalline Cannabidiol to stimulate the appetite of the patient, wherein the crystalline Cannabidiol is administered simultaneously or sequentially with a pharmaceutically effective amount of another agent useful for the treatment of cancer.

The term "pharmaceutically effective amount" as used herein, refers to that amount of solid Cannabidiol, such as the new form of crystalline Cannabidiol, which may include substantially pure forms thereof, that elicits the biological or medicinal response in a tissue system, animal or human that is being sought by a researcher, veterinarian, medical doctor or other clinician, which includes alleviation of the symptoms of the disease or disorder being treated. The specific pharmaceutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with crystalline Cannabidiol; and like factors well known to the researcher, veterinarian, medical doctor or other clinician of ordinary skill. For example, in animal studies, as set forth in U.S. Pat. No. 9,125,859, Cannabidiol prepared by non-synthetic methods was dosed at 50 and 100 mg/kg when delivered intra-peritoneally for the treatment of epilepsy and was effective in reducing mortality at said doses. When delivered for treatment, the formulation may contain solid Cannabidiol, such as the new form of crystalline Cannabidiol, which may include substantially pure forms thereof. When delivered for treatment, the formulation may contain Cannabidiol in a non-solid form, such as in a liquid state, wherein the Cannabidiol was sourced as a solid form, such as a crystalline form, an example being (R,R)-(−)-crystalline Cannabidiol or substantially pure (R,R)-(−)-crystalline Cannabidiol.

Having generally described the invention, reference to certain examples, which are provided herein for the purposes of illustration, and are not intended to be limiting unless otherwise specified, may be helpful to illustrate certain embodiments of the invention.

EXAMPLES

Example 1

Instrumentation

Chromatographic separation and purification were performed by a number of methods. Column chromatography and flash chromatography were performed using silica gel (Sorbent Technologies, Catalog number 52500-05). HPLC analyses were performed on a Hewlett Packard series 1100 HPLC instrument. Both Proton and Carbon NMR data were recorded on a Bruker 400 Ultrashield instrument (400 MHz and 100.6 MHz, respectively) BZH 377/400/70F, D 207/54-4146. The NMR spectra were taken in the indicated solvents and chemical shifts are reported in parts per million (ppm)

downfield from tetramethyl silane (TMS). Splitting patterns are reported as s, singlet; d, doublet; t, triplet; q, quartet; brs, broad singlet, and m, multiplet as appropriate. Infrared spectra (FTIR) were recorded on an Avatar 360 E.S.P. instrument over 32 scans (DTGS KBr Detector and a KBr Beamsplitter) and are reported in wavenumbers (cm$^{-1}$). Samples were prepared as neat solids. DSC (differential scanning calorimetry) data were obtained on a TA Instruments, DSC Q10. The samples were prepared by transferring 1 mg of the solid compound to a DSC aluminum pan (TA instruments part number 900786.901), covering it with an aluminum lid (TA instruments part number 900779.901) and then crimping the assembly together on a press. This assembly was equilibrated on the instrument at 35° C., 40° C., or 50° C. (Isothermal for 2.00 min) and was heated as indicated herein where the inflection point was experimentally determined and recorded. XRPD results were recorded on a Bruker D2 Phaser (24.6×1.0 mm zero diffraction plate). Melting points were obtained by preparing the samples in a glass capillary tube and running them on a Buchi Melting Point Model B-545 apparatus with a gradient of 0.5° C./min from 114° C. to 124° C. and are uncorrected. Optical rotation was measured on a Rudolph Research Analytical Autopol® V Automatic polarimeter with each reading time averaged over 2 seconds. The microcell size was 1 dm/2 mL with the indicated solvent and concentration (c), reported in grams of solute per 100 mL of solution at the sodium D line (589 nm).

TABLE 4

Bruker D2 Phaser XRPD Parameters

| Instrument Parameter | Value |
|---|---|
| Settings | |
| Radiation Anode | Cu |
| Generator Settings | 30 kV, 10 mA |
| Rotation (Variable Rot) | 15 rpm |
| Scan type | Coupled TwoTheta/Theta |
| Step Time (Time) | 5 seconds |
| Scan Range | Start: 4° and Stop: 40° |
| Step Size (Increment) | 0.01° |
| Air-Scatter Screen | 1 mm |
| LYNXEYE Detector (Solid Angle) | 3° detector opening |
| Primary Optics | |
| Divergence Slit | 0.6 mm |
| Soller Slit Module | 2.5° |
| Secondary Optics | |
| Anti-Scatter Slit | 3 mm |
| Soller Slit Module | 2.5° |
| Filter (Kβ) | Ni 2.5% |

Example 2

Preparation of 2-Hydroxy-4-oxo-6-pentyl-cyclohex-1-enecarboxylic acid ethyl ester, sodium salt (1)

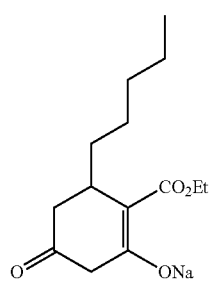

To a 2 L, 4-neck round bottom flask fitted with an overhead stirrer, thermometer, addition funnel, and a reflux condenser was added diethyl malonate (100.0 g, 94.8 mL, 0.624 mol, 1.11 eq). The solution was stirred at room temperature and a solution of 21% sodium ethoxide (221 mL) was added dropwise over 0.75 h where the internal temperature of the reaction mixture increased by 5° C. After the addition was complete, the stirred solution was heated to between 40° C.-55° C. (Target 45° C.) and 3-nonene-2-one (78.9 g, 93.1 mL, 0.56 mol, 1.00 eq) was added dropwise over 0.75 h where the internal solution temperature increased another 10° C. The solution was then heated to 65° C.-75° C. (Target 70° C.), where it was determined to be complete by the disappearance of 3-nonene-2-one by HPLC upon sampling the solution (typically 3 h and the product begins to precipitate from solution). It was then allowed to cool to room temperature overnight with stirring. The next day, the solution was cooled to 0° C. with stirring where it was allowed to stir for 7 h, and was then filtered at 0° C. The cake was washed with 150 mL of cold MTBE and was allowed to dry overnight in a vacuum drying oven at 40° C. This provided 126.9 g (82%) of product as a yellow to off-white solid. It could be carried on to the next step without any additional purification. m.p. 244° C. to 251° C. (by DSC, a small inflection is at 162° C). FT IR (cm$^{-1}$): 2924, 1701, 1576, 1351, 1297, 1218, 1045, 836, 718, 608 (key peaks). $^1$H NMR (400 MHz, D$_2$O): 4.31(q,2H, J=8 Hz); 3.29(d,1H,J=8 Hz); 2.53-2.40(m, 2H); 2.26-2.13(m,1H); 1.50-1.28(m,12H); 0.93(t,3H,J=8 Hz). $^{13}$C NMR (100.6 MHz, DMSO-d6): 190.4, 186.5, 173.0, 99.5, 59.2, 59.1, 40.6, 36.4, 34.2, 31.3, 25.3, 21.9, 14.2, 13.8.

Example 3

Preparation of 3,5-Dibromo-2,4-dihydroxy-6-n-pentyl-benzoic acid ethyl ester (Compound 2)

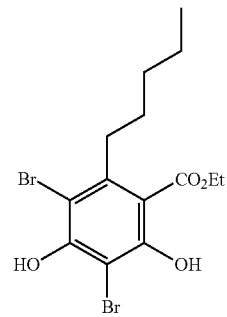 [SMILES: CCCCCc1c(Br)c(O)c(Br)c(O)c1C(=O)OCC]

To a 3 L, 3-neck flask with a thermometer, overhead stirrer, and an addition funnel was added compound 1 (91.8 g, 0.33 mol, 1.00 eq), sodium acetate (109 g, 1.33 mol, 4.0 eq) and acetic acid (462 mL). The solution was warmed to 45° C.-55° C. (target 45° C.) with stirring. Bromine (168 g, 53.7 mL, 1.05 mol, 3.18 eq) was added dropwise over 3 h at a rate where the internal solution temperature was maintained between 45° C.-55° C. (target 50° C.). As time and temperature increased, the solution became homogeneous. After the addition was completed, the solution was stirred for an additional 1.25 h at 45° C.-55° C., an aliquot was removed and the reaction was deemed complete by HPLC. The solution was then cooled to room temperature. Water, 900 mL, was added dropwise to the stirring solution over 0.75 h and the product began to precipitate from solution after about 450 mL of water were added. After the water addition was complete, the solution was cooled to 15° C.-20° C. and the solids were filtered and washed with water to yield 110.7 g (80%), which was of acceptable quality to take onto the next step without any additional purification. It needs to be noted that about 3% water remains, about 3% residual acetic acid, about 5% salts, and traces of mono bromo ethyl olivetolate and ethyl olivetolate are present. An analytically pure sample was prepared by dissolution of the solid in 10 volumes of hot heptane and filtering the solids upon cooling to 0° C. m.p. 69° C.-71° C. (heptane by DSC) lit=67° C. (Korte, Friedhelm, *Annalen der Chemie, Justus Liebigs* 1960, V630, pp. 71-83). FT IR (cm$^{-1}$): 3471(br), 2962, 2933, 2858, 1654, 1562, 1468, 1391, 1369, 1289, 1215, 1127, 1065, 1018, 875, 797, 700, 673 (partial reporting). $^1$H NMR (400 MHz, CDCl$_3$): 12.3(s,1H); 6.5(s,1H); 4.46(q,2H, J=8 Hz); 3.13-3.09(m,2H); 1.6-1.44(m,4H); 1.42-1.3(m,5H); 0.93(t,3H, J=8 Hz) $^{13}$C NMR (100.6 MHz, DMSO-d6): 170.8, 159.9, 154.1, 145.1, 107.6, 105.3, 96.8, 62.6, 36.0, 32.3, 29.4, 22.6, 14.2 (2).

Example 4

Preparation of 2,4-Dihydroxy-6-n-pentyl-benzoic acid ethyl ester (Compound 3)

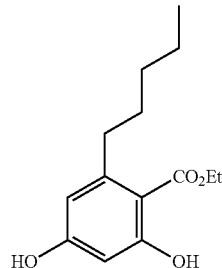 [SMILES: CCCCCc1cc(O)cc(O)c1C(=O)OCC]

To a 2 L Parr stirring pressure vessel was added compound 2 (75.0 g, 0.18 mol, 1.0 eq), sodium citrate (98.4 g, 0.46 mol, 2.6 eq), 10% palladium on carbon (wet 50% water, 11.7 g), water (210 mL), ethanol (140 mL). The vessel was sealed and flushed with nitrogen and subsequently was pressurized with hydrogen (5 atm) with rapid stirring as stirring rate affects the reaction rate. The solution was heated to 55° C.-65° C. and it was allowed to stir at this temperature for 14 h. The solution was sampled and the reaction was complete by HPLC. The reactor was then cooled to room temperature and was flushed with nitrogen. The solution was filtered through a 75 g celite pad and the pad was washed with 150 mL of a (1:1) toluene water solution. The resulting solution was then partitioned in a separatory funnel and the toluene solution containing the product was concentrated to contain about 30 mL of toluene plus the product. Heptane (160 mL) was added and the solution was concentrated to about 60 mL (total volume including the product). Another 25 mL portion of heptane was added and the organic layer contained NMT 1% toluene by weight. The solution temperature was kept at or above 30° C. over the solvent swapping operation. The solution was then warmed briefly to 50° C. or greater to ensure complete dissolution of any crystalline material and was then cooled to 0° C. over 2 h. The solution was allowed to stir another 2 h at 0° C. and it was filtered at that temperature. The cake was washed with cold (0° C.) heptane (30 mL) and was allowed to dry in a vacuum drying oven at room temperature for 24 h to afford 32 g of compound 3 (71% unadjusted) as a yellow-orange solid. m.p. 67° C.-69° C. (heptane by DSC), lit=69° C. (Korte, Friedhelm, *Annalen der Chemie, Justus Liebigs* 1960, V630, pp. 71-83). FT IR (cm$^{-1}$): 3339 br, 2953, 2928, 2860, 1639, 1581, 1366, 1314, 1256, 1213, 1174, 1105, 1015, 837, 712, 673, 620 (partial reporting). $^1$H NMR (400 MHz, CDCl$_3$): 11.79 (s,1H); 6.27(d,1H, J=2 Hz); 6.22(d,1H, J=2 Hz); 5.5-5.1 (brs,1H); 4.40(q,2H, J=8 Hz); 2.87-2.83 (m,2H); 1.75-1.45(m, 4H); 1.41(t,3H, J=8 Hz); 1.38-1.28(m, 2H); 0.89(t,3H, J=8 Hz). $^{13}$C NMR (100.6 MHz, DMSO-d6): 171.9, 165.4, 160.6, 149.2, 111.1, 105.4, 101.7, 61.6, 37.2, 32.3, 31.9, 22.9, 14.4, 14.3.

Example 5

Preparation of Crystalline (R,R)-(−)-Cannabidiol (Compound 5) by Seeding

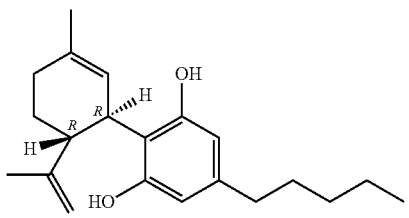

To a 1 L round bottom 4-neck flask with a mechanical stirrer, a thermometer, and two addition funnels was added compound 3 (30.0 g, 119 mmol, 1.00 eq) and sodium sulfate (5.91 g, 41.6 mmol, 0.35 eq) followed by addition of dichloromethane (225 mL). The solution was cooled to −15° C. to −10° C. and 2 separate solutions of borontrifluoride diethyl etherate complex (6.59 g, 5.73 mL, 46.4 mmol, 0.39 eq) in one dropping funnel and (+)-Para-Mentha-2,8-Diene-1-ol (28.06 g, 30.2 mL, 184.3 mmol, 1.55 eq) were added simultaneously over 2 h keeping the temperature between −15° C. and −10° C. at a rate where each reagent was simultaneously exhausted. The solution was allowed to stir at −15° C. to −10° C. for an additional 3 h. The reaction was then quenched with 5% aqueous sodium hydroxide and was allowed to stir and warm to room temperature over 4 h/overnight. The layers were partitioned in a separatory funnel and dichloromethane layer was washed with 90 mL of a sat. aq. KHCO$_3$ solution and was concentrated to an oil. Ethanol (200 mL) was added and the solution was concentrated again to remove all the dichloromethane present. The total volume of the crude intermediate in residual ethanol containing no dichloromethane was approximately 60 mL. To this solution ethanol (200 mL) was added. A solution of lithium hydroxide (3.57 g, 149 mmol, 1.25 eq) in water (79 mL) followed by addition of heptane (90 mL) were added with vigorous stirring. After the solution was allowed to stir at room temperature for 1 h and the layers were separated and the heptane layer was discarded. A solution of 10% aqueous lithium hydroxide (90 mL) was added, the solution was degassed and was heated where 60 mL of ethanol was removed and replaced with 60 mL of methanol. The solution was then heated to reflux for 24-48 h until the reaction was proven to be complete by HPLC analysis. The solution was then cooled to about 10° C.-15° C. and was acidified to pH 5 to 6 with approximately 120 mL of 47% aqueous citric acid. The product was extracted with 120 mL of a Heptane: MTBE (4:1) solution and then with a second 60 mL portion of Heptane:MTBE (4:1). The combined organic layers were washed with saturated aq. KHCO$_3$ (60 mL), which was followed with a second wash with a saturated aq. Na$_2$SO$_4$ solution. This solution was filtered through a plug (prepared by addition to a 4 inch diameter fritted glass filter of 30 g celite, then 30 g silica gel, then 15 g activated charcoal, then 15 g celite) and the plug was then washed with 60 mL of dry MTBE. The solvents were concentrated to ensure complete removal of MTBE where the total volume of the solution was 66 mL. The solution was then cooled to 0° C. and it was seeded with 100 mg of crystalline Cannabidiol (prepared as shown in Example 6). The solution was then placed in a freezer overnight at −35° C. where the product crystallized. The solution was removed from the freezer and placed in an acetonitrile/dry ice bath where it was stirred with a Teflon stir bar for 3 h at −35° C. as measured by an internal thermometer. The solution was then filtered cold and was washed with 18 mL of cold (−35° C.) heptane. The solids were allowed to dry overnight in a vacuum drying oven at 22° C. to give 17.9 g of product (48% from 3) that was greater than 99 (a/a) % pure by HPLC. m.p. 43° C.-47° C. (heptane by DSC). FT IR (cm$^{-1}$): 3369 br, 2956, 2926, 2857, 1628, 1585, 1519, 1433, 1377, 1308, 1240, 1026, 960, 890, 864, 847, 829, 800, 658, 619 (partial reporting). $^1$H NMR (400MHz, CD$_3$OD): 6.06 (s,2H); 5.27(s,1H); 4.45(s,1H); 4.41(s,1H); 3.95-3.87(m,1H); 2.92-2.83(m,1H); 2.36(t,2H, J=8Hz); 2.28-2.13(m,1H); 2.05-1.93(m,1H); 1.76-1.68(m, 2H); 1.66(s,3H); 1.62(s,3H) 1.60-1.49(m,2H); 1.38-1.21(m, 4H); 0.89(t,3H, J=8 Hz). $^{13}$C NMR (100.6 MHz, CD$_3$OD): 157.6, 150.4, 142.9, 134.7, 127.4, 116.1, 110.6, 108.5, 46.6, 37.6, 36.7, 32.7, 32.1, 31.8, 30.8, 23.8, 23.7, 19.7, 14.5. [Alpha]$^{25}_D$=−121 (c=1.00, ethyl acetate). Reported as −125 by Ben-Shabat, et. al. *J. Med. Chem.* 2006, 49, 1113-1117 for the naturally occurring (−) isomer (R,R). The percent enantiomeric excess of the material was found to be greater than 99% by chiral HPLC analysis employing the method listed in the *Journal of Chromatography A,* 679 (1994) pp. 47-58.

Example 6

Preparation of Amorphous Cannabidiol Followed by Preparation of the Seeds of the Original New Polymorph (m.p. 43° C.-47° C.)

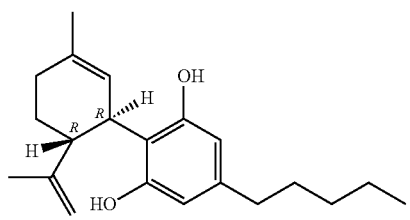

To a 250 mL 3-neck round bottom flask fitted with a nitrogen adapter, a thermometer, and a Teflon stir bar was added compound 3 (12 g, 47.6 mmol, 1.00 eq), magnesium sulfate (3.21 g, 26.7 g, 0.56 eq), and (+)-Para-Mentha-2,8-Diene-1-ol (7.42 g, 48.8 mmol, 1.025 eq) (Obiter Labs). The solution was cooled to 0° C. to 10° C. in an ice water bath and solid scandium triflate (1.22 g, 2.48 mmol, 0.052 eq). The solution was allowed to stir at this temperature for about 7 h, at which time HPLC analysis indicated that the reaction was no longer progressing. The solution was filtered through a celite plug and concentrated to an oil and the dichoromethane solvent was replaced with 300 mL of heptane by trituration. The heptane solution containing product was washed with 2×200 mL portion of 30% aqueous NaOH to remove unreacted starting material and the heptane layer was dried over solid sodium sulfate, filtered through celite and concentrated to an oil, which was further purified by column chromatography to give two lots of material. One lot was 9.2 g, which was greater than 90% pure and the other fractions 4.91 g were greater than 95% pure. The 4.91 g portion (~12.5 mmol) was dissolved in methanol (30 mL) and 30 mL of 50% aqueous NaOH was added. This solution was degassed and was heated to reflux for 26 h, at which time the remaining starting material was less than 2%. The solution was then cooled to room temperature and toluene (40 mL) was added and the solution was acidified to pH 4 with 50% aqueous citric acid. The layers were separated and the toluene solution was concentrated and heptane was added (48 mL). This solution was concentrated to an oil and the process was repeated to remove residual toluene. The oil was then chromatographed with 300 g of silica gel using a 3" diameter column by using a mobile phase of 15% toluene in heptane several fractions were collected and the most pure ones were combined to 0.70 g of Cannabidiol as an oil at 99.6% purity by HPLC. This material would not crystallize by repeated attempts to dissolve it heptane or pentane with cooling. Therefore, it was distilled by a bulb to bulb distillation (0.1 torr, 120° C. pot temperature) to yield 0.68 g of product at a slightly reduced purity level of ~97% (a/a) by HPLC. This material was cooled to −35° C. in a freezer and removed. To the cold surface was added 1 mg of solid crystalline Cannabidivarin as prepared according to Example 7 plus about 4 drops of cold pentane. The material was placed in the freezer overnight. The next day there was a thin film of crystalline material over the glassy oily substance. The crystals were carefully removed and were propagated by taking the other purified fractions of Cannabidiol (0.50 to 74 g) dissolved in heptane (1-2 mL) at 0° C., seeding the solution, and cooling the mixtures to −35° C. where more crystals appeared. This seeding/crystallization process could be repeated to produce material of a similar XRPD pattern without any added crystalline Cannabidivarin for all future lots. The physical properties of this material are essentially identical to those reported for example 5 in the text. The DSC and XRPD of the seminal lot of seed crystals is found in FIGS. 5 and 7.

Example 7

Preparing Seed Crystals of Crystalline Cannabidivarin

All chemicals employed were from Sigma-Aldrich unless otherwise noted. To a nitrogen filled 500 mL 3-neck flask with a dropping funnel, thermometer, a nitrogen inlet, and a teflon magnetic stir bar was added 2,4-Dihydroxy-6-propyl-benzoic acid ethyl ester (ethyl varinolate, lot DAD-004-165) (7.35 g, 32.8mmol, 1.00 eq.); dichloromethane (66 mL); magnesium sulfate (2.21 g, 18.4 mmol, 0.56 eq), and scandium triflate (Strem, Inc.) (0.84 g,1.71 mmol, 0.052 eq). The solution was cooled to 10° C. with the aid of an ice-water bath. A solution of (+)-PMD (Obiter Labs—Champaign, Ill.) (4.99 g, 5.37 mL, 32.8mmol, 1.00 eq) dissolved in dichloromethane (21 mL) was added dropwise over 5-10 minutes with rapid stirring keeping the internal temperature of the flask below 15° C. The solution was allowed to stir at 5° C.-15° C. for 5.5 h, by which time the reaction was no longer progressing by HPLC analysis. The reaction was then quenched with the addition of solid sodium carbonate (0.84 g, 7.9 mmol, 0.24 eq) at 5° C.-15° C., the cooling bath was removed and the solution was allowed to warm to ambient temperature where it was allowed to stir for 3 h. The solids were removed by filtration through a celite plug, which was washed with 20 mL of dichloromethane, and the resulting solution was concentrated in vacuo to an oil. Heptane (100 mL) was added and the solution was again concentrated to an oil. The resulting oil was dissolved in heptane (150 mL) and it was extracted with 2×45 mL portions of a 20% aqueous sodium hydroxide solution. The heptane layer was dried over sodium sulfate and was concentrated to give 10.11 g of a crude oil (80%, unadjusted) at approximately 80-90% pure by proton NMR. A portion of this material, 0.94 g, was then subjected to column chromatography by eluting it on a 1" diameter column filled with 50 g of silica gel with a mixture of hexane:toluene (4:1, respectively). The most pure fractions by TLC were combined to provide ethyl cannabidivarinolate (0.54 g) at approximately 99% purity, by HPLC at 224 nm, as an oil. It was then added to a 25 mL round bottom flask and methanol, 3.6 mL, and 50% aqueous sodium hydroxide, 3.6 mL were then added. The stirring solution was degassed under vacuum and placed under a nitrogen atmosphere where it was heated to reflux for 5.5 h, at which time it was shown to be complete by HPLC analysis. The solution was then cooled to room temperature where it was acidified to pH 5 with a 50% aqueous citric acid solution and the product was extracted with toluene (20 mL). The toluene layer was dried over sodium sulfate, 2 g, and was concentrated to an oil. This oil was chromatographed 3 times on a 1" diameter column containing 20 g of silica gel as the solid phase and a toluene:heptane mixture (4:1) as the eluting solvent to yield 0.13 g of cannabidivarin as an oil in greater than 99% purity by HPLC upon concentration. The oil was dissolved in heptane (5 mL) and was concentrated again to 0.13 g. The process was repeated a second time and pentane (2 drops) was added to the oil where it was allowed to stand in a sealed container overnight at −35° C. The next day, crystals were present and a small portion was removed 0.04 g, which was determined to be crystalline by XRPD. m.p. 118° C.

A sample of non-crystalline Cannabidivarin was removed from its storage container and was allowed to warm to about 5° C. at which temperature the solution became homogeneous. It was seeded with about 1 mg of solid crystalline Cannabidivarin made as described above in this Example. The solids propagated in solution and they were removed by filtration to yield 70 mg of crystalline Cannabidivarin with a melting point of 120° C. This material was then used as seed crystals in Example 6.

Example 8

Prophetic Example for Making Amorphous Cannabidiol

Amorphous Cannabidiol is made by rapid precipitation of a solution made from purified new form of crystalline Cannabidiol and a solvent by adding the solution to an antisolvent with significant agitation. It may be (R,R)-(−)-Cannabidiol such as substantially pure (R,R)-(−) Cannabidiol Example 9

Prophetic Example for Making Amorphous Cannabidiol

A solution made by dissolving purified new form of crystalline Cannabidiol is rapidly spray dried to prepare amorphous Cannabidiol.

We claim:
1. A crystalline form of Cannabidiol having a melting point within the range of from 37° C. to 50° C.
2. The crystalline Cannabidiol of claim 1 having a melting point within the range of from 43° C. to 47° C.
3. The crystalline Cannabidiol of claim 2 having a powder x-ray diffraction pattern comprising a peak at about 10.7° 2θ.
4. A crystalline form of Cannabidiol having a powder x-ray diffraction pattern comprising a peak at about 10.7° 2θ.
5. The crystalline Cannabidiol of claim 4, which is crystalline (R,R)-(−)-Cannabidiol.
6. The crystalline Cannabidiol of claim 4 having a powder x-ray diffraction pattern comprising a peak at about 14.8° 2θ.
7. The crystalline Cannabidiol of claim 4 having a powder x-ray diffraction pattern comprising a peak at about 21.4° 2θ.
8. The crystalline Cannabidiol of claim 4 having a powder x-ray diffraction pattern comprising a peak at about 29.9° 2θ.
9. The crystalline Cannabidiol of claim 4 having a powder x-ray diffraction pattern comprising a peak at each of the following positions: about 10.7° 2θ, about 14.8° 2θ and about 21.4° 2θ.
10. The crystalline Cannabidiol of claim 4 having a differential scanning calorimetry thermogram comprising a maximum endotherm at from 43° C. to 47° C., wherein the differential scanning calorimetry thermogram has a temperature ramp rate of 1° C. per minute.
11. The crystalline Cannabidiol of claim 4 having an FT-IR spectrum comprising a peak at one or more of the following positions: about 658 $cm^{-1}$, about 890 $cm^{-1}$, about 1026 $cm^{-1}$, about 1433 $cm^{-1}$, about 1585 $cm^{-1}$, about 1628 $cm^{-1}$ and about 2926 $cm^{-1}$.
12. A pharmaceutical formulation comprising crystalline Cannabidiol of claim 4 and one or more pharmaceutically acceptable excipients.
13. A process for making crystalline Cannabidiol of claim 4, which comprises:
providing a solution of Cannabidiol in a suitable solvent;
contacting the solution of Cannabidiol with an antisolvent to form a mixture; and
removing the suitable solvent from the mixture in the presence of seed crystals under conditions sufficient to make the crystalline Cannabidiol.
14. The process of claim 13, wherein the seed crystals are crystalline Cannabidiol, and wherein the crystalline Cannabidiol seed crystals have a melting point within the range of from 43° C. to 47° C., or have a powder x-ray diffraction pattern comprising a peak at about 10.7° 2θ, or have both a melting point within the range of from 43° C. to 47° C. and a powder x-ray diffraction pattern comprising a peak at about 10.7° 2θ.
15. The process of claim 13, wherein the seed crystals are crystalline Cannabidivarin, and wherein the crystalline Cannabidivarin seed crystals have a powder x-ray diffraction pattern comprising a peak at one or more of the following positions: about 9.4° 2θ, about 11.7° 2θ, about 14.4° 2θ, about 15.5° 2θ, and about 17.1° 2θ.
16. The crystalline Cannabidiol of claim 4, which is greater than 99 (a/a) % pure as determined by HPLC.

* * * * *